US011590184B2

(12) United States Patent
Alkayyal et al.

(10) Patent No.: US 11,590,184 B2
(45) Date of Patent: Feb. 28, 2023

(54) ONCOLYTIC RHABDOVIRUS EXPRESSING IL12

(71) Applicant: TURNSTONE LIMITED PARTNERSHIP, Toronto (CA)

(72) Inventors: Almohanad Alkayyal, Ottawa (CA); Rebecca Auer, Ottawa (CA); John Cameron Bell, Ottawa (CA)

(73) Assignee: TURNSTONE LIMITED PARTNERSHIP, Toronto (CA)

( * ) Notice: Subject to any disclaimer, the term of this patent is extended or adjusted under 35 U.S.C. 154(b) by 883 days.

(21) Appl. No.: 16/324,490

(22) PCT Filed: Aug. 9, 2017

(86) PCT No.: PCT/CA2017/050941
§ 371 (c)(1),
(2) Date: Feb. 8, 2019

(87) PCT Pub. No.: WO2018/027316
PCT Pub. Date: Feb. 15, 2018

(65) Prior Publication Data
US 2019/0216868 A1 Jul. 18, 2019

Related U.S. Application Data

(60) Provisional application No. 62/372,406, filed on Aug. 9, 2016.

(51) Int. Cl.
| | |
|---|---|
| *A61K 35/766* | (2015.01) |
| *A61K 9/00* | (2006.01) |
| *C12N 5/10* | (2006.01) |
| *C07K 14/145* | (2006.01) |
| *C12N 15/86* | (2006.01) |
| *A61K 38/20* | (2006.01) |
| *A61P 35/00* | (2006.01) |
| *C07K 14/54* | (2006.01) |
| *A61K 35/768* | (2015.01) |

(52) U.S. Cl.
CPC .......... *A61K 35/766* (2013.01); *A61K 9/0019* (2013.01); *A61K 35/768* (2013.01); *A61K 38/20* (2013.01); *A61K 38/208* (2013.01); *A61P 35/00* (2018.01); *C07K 14/145* (2013.01); *C07K 14/54* (2013.01); *C07K 14/5434* (2013.01); *C12N 5/10* (2013.01); *C12N 15/86* (2013.01); *C12N 2760/20041* (2013.01); *C12N 2760/20232* (2013.01); *C12N 2760/20243* (2013.01)

(58) Field of Classification Search
None
See application file for complete search history.

(56) References Cited

U.S. PATENT DOCUMENTS

2005/0260601 A1 11/2005 Whitt et al.

FOREIGN PATENT DOCUMENTS

EP 2510088 A2 10/2012

OTHER PUBLICATIONS

Yang, et al. (2014) "Combined Therapy with Cytokine-Induced Killer Cells and Oncolytic Adenovirus Expressing IL-12 Induce Enhanced Antitumor Activity in Liver Tumor Model", PLOS One, 7(9): e44802, 11 pages long. (Year: 2014).*
Vandendriessche, 2012, "Outstanding Achievement Award—Addressing the bottlenecks in gene therapy through synthetic biology and de novo vector design," European Society of Gene and Cell Therapy French Society of Cell and Gene Therapy Collaborative Congress 2012, Oct. 25-29, 2012, Versailles, France (173 pages).
International Search report and Written Opinion dated Oct. 31, 2017 in PCT Application No. PCT/CA2017/050941.
Alkayyal, Almohanad A., et al. "NK-cell recruitment is necessary for eradication of peritoneal carcinomatosis with an IL 12-expressing Maraba virus cellular vaccine." Cancer immunology research, Feb. 3, 2017.
Alkayyal, A. et al., "Oncolytic Rhabdo Virus MG 1-IL12 Enhances Anti-tumour Immunity". Ottawa Hospital Research Institute 2013 Research Day, Nov. 14, 2013, pp. 12-13, (abstract) Retrieved on Oct. 23, 2017 from URL: http://www.ohri.ca/newsroom/photos/uploads/researchdaybooklet2013.pdf.
Lemay, Chantal G., et al. "Harnessing oncolytic virus-mediated antitumor immunity in an infected cell vaccine." Molecular Therapy, vol. 20, No. 9, pp. 1791-1799, Sep. 1, 2012.
Lichty, Brian D., et al. "Going viral with cancer immunotherapy." Nature Reviews Cancer, vol. 14, No. 8, p. 559, Aug. 2014.

(Continued)

*Primary Examiner* — Robert M Kelly
(74) *Attorney, Agent, or Firm* — Jones Day

(57) ABSTRACT

Disclosed herein is an oncolytic recombinant Maraba virus whose genome comprises one or more nucleic acid sequences that, in combination, encode an interleukin-12 (IL12) protein or a functional portion thereof. A method for treating a cancer in a patient using the oncolytic recombinant Maraba virus is also disclosed. The present disclosure also provides a tumour cell infected with an oncolytic rhabdovirus whose genome comprises one or more nucleic acid sequences that, in combination, encode an interleukin-12 (IL12) protein or a functional portion thereof, for use as an infected cell vaccine (ICV) for the treatment of a cancer. A method for treating a cancer in a patient using the infected cell vaccine is also disclosed.

34 Claims, 21 Drawing Sheets
Specification includes a Sequence Listing.

(56) References Cited

OTHER PUBLICATIONS

Shin, Edward J., et al. "Interleukin-12 expression enhances vesicular stomatitis virus oncolytic therapy in murine squamous cell carcinoma." The Laryngoscope, vol. 117, No. 2, pp. 210-214, Feb. 2007.

Zhang, Jiqing, et al. "Maraba MG1 virus enhances natural killer cell function via conventional dendritic cells to reduce postoperative metastatic disease." Molecular Therapy, vol. 22, No. 7, pp. 1320-1332, Jul. 1, 2014.

\* cited by examiner

ONCOLYTIC RHABDOVIRUS EXPRESSING IL12

RELATED APPLICATIONS

This application is a United States National Phase under 35 U.S.C. § 371 of International Application No. PCT/CA2017/050941, filed on Aug. 9, 2017, which claims priority to, and the benefit of U.S. Provisional Patent Application No. 62/372,406 filed Aug. 9, 2016, the entire contents of both of which are hereby incorporated by reference.

SEQUENCE LISTING

The instant application contains a Sequence Listing, which has been submitted electronically in ASCII format and is hereby incorporated by reference in its entirety. Said ASCII copy, created on Feb. 5, 2019, is named pctca2017050941-seql.txt and is 12.0 KB in size.

FIELD

The present disclosure relates to recombinant oncolytic rhabdoviruses expressing interleukin-12.

BACKGROUND

The following paragraphs are not an admission that anything discussed in them is prior art or part of the knowledge of persons skilled in the art.

Oncolytic Viruses (OVs) are promising anti-cancer therapeutics engineered or selected to infect and multiply in tumour cells while having attenuated replication capacity in normal tissues. One feature important to the efficacy of some OVs is the ability to stimulate an anti-tumour immune response.

Vaccination of patients with their own cancer cells (autologous cell vaccine) has been tried in the past with variable success (1, 2). Most have employed mixing the whole cell vaccine with non-specific adjuvants, such as *Bacillus* Colmette-Guérin (BCG), but difficulties in overcoming immune suppression within the tumour microenvironment have yielded limited results (3). Nonetheless, clinical trials have consistently shown that survival is significantly better in those patients that are able to mount an immune response to the whole cell vaccine, suggesting that when an immune response is generated, prognosis is improved (4).

Cytokines, such as IL-12 have also been used to direct an anti-tumour immune response but the short half-life of these cytokines, when administered as proteins, and the dose-limiting toxicities encountered following systemic administration have diminished their potential effectiveness (5). That said, the strong immunological rationale for cytokine based vaccines continues to drive the development of novel experimental approaches in numerous laboratories worldwide.

INTRODUCTION

The following introduction is intended to introduce the reader to this specification but not to define any invention. One or more inventions may reside in a combination or sub-combination of the elements or method steps described below or in other parts of this document. The inventors do not waive or disclaim their rights to any invention or inventions disclosed in this specification merely by not describing such other invention or inventions in the claims.

A common problem in the use of oncolytic viruses for treatment of cancer is insufficient anti-tumour immune activation using the virus as a single agent.

There is a need in the field for means of treating cancer with OVs capable of anti-tumour immune activation. Such OVs may be used in an autologous cell vaccine having an improved immune response in the tumour microenvironment.

In one aspect, the present disclosure attempts to address or ameliorate one or more shortcomings involved with the oncolytic virus treatment of cancer by providing a Maraba virus whose genome includes a nucleic acid sequence that encodes, or nucleic acid sequences that encode, interleukin-12 (IL12) or a functional portion thereof. Expression of the IL12 protein or functional portion thereof may enhance the immunogenicity of tumour cells infected with the Maraba virus.

Interleukin 12 is also known as natural killer cell stimulatory factor (NKSF) or cytotoxic lymphocyte maturation factor (CLMF). IL-12 is a heterodimeric cytokine containing two disulfide-linked subunits, p35 and p40. The sequences of the human p35 and p40 proteins are shown in SEQ ID NOs: 1 and 2, respectively. The sequences of the murine p35 and p40 proteins are shown in SEQ ID NOs: 3 and 4, respectively. Human and murine IL-12 share 60% and 70% amino acid sequence identity in their p35 and p40 subunits, respectively. The disulfide-linked murine p40 homodimer can bind to IL-12 receptors and can act as an antagonist of IL-12 activities in vitro. The murine p40 monomer may still act as an IL-12 antagonist, though at a reduced activity in comparison to the activity of the homodimer. In the context of the present disclosure, such monomers and homodimers of p40 would be considered to be functional portions of IL12.

The IL12 or functional portion thereof encoded by the Maraba virus may have sequences that substantially correspond to the human p35 and p40 sequences. The IL12 or functional portion thereof encoded by the Maraba virus may have sequences that substantially correspond to the murine p35 and p40 sequences. The IL12 or functional portion thereof encoded by the Maraba virus may have a sequence that is at least 60% identical to the wildtype human IL12, so long as the IL12 or functional portion thereof is able to: stimulate growth of T cells, NK cells, or both; enhance the lytic activity of human NK/lymphokine-activated killer cells; stimulate the production of IFN-gamma by resting human peripheral blood mononuclear cells (PBMCs); or any combination thereof.

The IL12 may have a sequence that is a chimera of sequences of IL12 from different origins. For example, the IL12 encoded by the Maraba virus may have a sequence that substantially corresponds to the sequence of the human p35 monomer, and a sequence that substantially corresponds to the sequence of the murine p40 monomer. The resulting heterodimer is a chimera of human and mouse IL12 subunits. As illustrated in the examples, murine IL12 expressed by a Maraba virus retains its stimulative properties with human NK cells despite the murine IL12 and human IL12 sharing only 70% and 60% amino acid sequence identity in their p40 and p35 subunits, respectively.

In the context of the present disclosure, expressions such as 'the IL12 sequence' should be understood to refer to the totality of the sequences of the subunits making up the dimeric protein, regardless of what order the subunits are listed in. Accordingly, it should be understood that the discussion above about the IL12 encoded by the Maraba virus having a sequence that is at least 60% identical to the wildtype human IL12 compares the combination of sequences of p35 and p40 encoded by the Maraba virus with the combination of sequences of p35 and p40 of the wildtype human IL12.

The rhabdovirus may be a variant of wildtype Maraba virus. The wildtype Maraba virus genome has a nucleotide sequence that encodes, from the 3' end to the 5' end, an N, a P, an M, a G and an L protein. Maraba virus (SEQ ID Nos: 1-6 of U.S. Pat. No. 8,481,023, incorporated herein by reference; HQ660076.1) A variant of wildtype Maraba virus according to the present disclosure may have a genome that has a nucleotide sequence that encodes the N, P, M, G and L proteins in a different order than 3'-N, P, M, G, L-5'. A variant of Maraba virus may include: a mutation of the G protein at a position corresponding to position 242 of the wildtype sequence such as Q242R; and/or a mutation of the matrix (M) protein at a position corresponding to position 123 of the wildtype sequence such as L123W. A variant of wildtype Maraba virus that includes both the Q242R mutation in the wildtype G protein, and the L123W mutation in the wildtype M protein, may be referred to herein as "MG1". A Maraba virus containing a substitution at amino acid 242 of the G protein and/or at amino acid 123 of the M protein as described at col. 2, lines 24-42 of U.S. Pat. No. 9,045,729, the entire contents of which are incorporated herein by reference. The oncolytic Maraba MG1 virus has been genetically modified with mutations in both the G and M proteins that make it hyper virulent in cancer cells with attenuation in normal cells (6). A variant of wildtype Maraba virus may include both a genome having a nucleotide sequence with re-ordered N, P, M, G and L proteins, and one or both of the mutations of the G and M proteins discussed above.

The IL12 may be encoded by one or more nucleotide sequences that are positioned: before the nucleotide sequences encoding the N, P, M, G and L proteins; after the nucleotide sequences encoding the N, P, M, G and L proteins; or in between any of the nucleotide sequences encoding the N, P, M, G and L proteins. For example, a nucleotide sequence encoding both the p35 and p40 proteins may be positioned between the nucleotide sequences encoding a mutated G protein and an L protein. In another example, a nucleotide sequence encoding p35 may be positioned between the nucleotide sequences encoding an M protein and a mutated G protein, while a nucleotide sequence encoding the p40 protein may be positioned between the nucleotide sequences encoding the mutated G protein and an L protein.

For clarity, it should be understood that the present disclosure contemplates any combination of: (i) changing the order of the proteins encoded by a Maraba virus; (ii) including mutations in the G and/or M proteins, as described above; and (iii) changing the position of the nucleotide sequence or sequences encoding IL12 or a functional portion thereof.

In another aspect, the present disclosure provides an infected cell vaccine (ICV) where tumour cells from a patient are infected with an oncolytic rhabdovirus expressing IL12 or functional portion thereof. In an infected cell vaccine, tumour cells are removed from a patient and infected with the oncolytic rhabdovirus in vitro. The virus infected cells may then be administered to the patient as the Infected Cell Vaccine (ICV). The oncolytic rhabdovirus may be a Maraba virus whose genome includes a nucleic acid sequence that encodes interleukin-12 (IL12) or functional portion thereof, as discussed herein. The ICV may be administered intraperitoneally; intravenously; intranasally, intracranially, subcutaneously, intrathecally, intradermally, intrathoracically or intramuscularly.

For clarity, it should be understood that the present disclosure contemplates that the IL12 or functional portion thereof expressed by the oncolytic rhabdovirus may be the same as the IL12 or functional portion thereof expressed by the Maraba virus discussed above.

For clarity, it should also be understood that the present disclosure contemplates any combination of: (i) changing the order of the proteins encoded by a wildtype rhadovirus; and (ii) positioning the nucleotide sequence or sequences encoding IL12 or a functional portion thereof between any of the genes encoding the rhabdovirus proteins.

In other aspects, the present disclosure provides a method for treating a cancer by administration of the disclosed Maraba virus, or the disclosed infected cell vaccine. The present disclosure also provides the corresponding use of the disclosed Maraba virus, or the disclosed infected cell vaccine, for treating a cancer.

BRIEF DESCRIPTION OF THE DRAWINGS

Embodiments of the present disclosure will now be described, by way of example only, with reference to the attached Figures.

FIG. 1 is a diagram that shows the insertion of the IL12 gene between the G and L genes of MG1 to form a recombinant MG1-IL12 oncolytic rhabdovirus.

FIG. 2 is an example demonstrating that the recombinant MG1 expressing IL12 is as cytotoxic to B16F10 tumour cells at the indicated MOIs as MG1 alone.

FIG. 3 is an example demonstrating that the recombinant MG1 expressing IL12 is as cytotoxic to CT26lacZ tumour cells at the indicated MOIs as MG1 alone.

FIG. 4 shows that an exemplary ICV comprising irradiated B16F10 tumour cells infected with recombinant MG1-IL12 produce the IL12 cytokine as measured by ELISA.

FIG. 5 shows that an exemplary ICV comprising irradiated CT26lacZ tumour cells infected with recombinant MG1-IL12 produce the IL12 cytokine as measured by ELISA.

FIG. 6 demonstrates that lung homogenates of tumour naïve mice administered an exemplary ICV comprising irradiated B16F10 tumour cells infected with recombinant MG1-IL12 have increased levels of the IL12 cytokine as measured by ELISA.

FIG. 7 demonstrates that lung homogenates of tumour naïve mice administered an exemplary ICV comprising irradiated B16F10 tumour cells infected with recombinant MG1-IL12 have increased levels of the IFNγ cytokine as measured by ELISA.

FIG. 8 shows the total number of $CD3^+$ T cells does not change in lungs of tumour naïve mice treated with an exemplary ICV comprising irradiated B16F10 tumour cells infected with recombinant MG1-IL12 as measured by flow cytometry.

FIG. 9 shows the total number of $NK1.1^+$ cells increases in lungs of tumour naïve mice treated with an exemplary ICV comprising irradiated B16F10 tumour cells infected with recombinant MG1-IL12 as measured by flow cytometry.

FIG. 10 shows the total number of $NK1.1^+$ IFNγ+ cells increases in lungs of tumour naïve mice treated with an exemplary ICV comprising irradiated B16F10 tumour cells infected with recombinant MG1-IL12 as measured by flow cytometry.

FIG. 11 shows the total number of NK1.1+ granzymeB+ cells increases in lungs of tumour naïve mice treated with an exemplary ICV comprising irradiated B16F10 tumour cells infected with recombinant MG1-IL12 as measured by flow cytometry.

Figure 18:
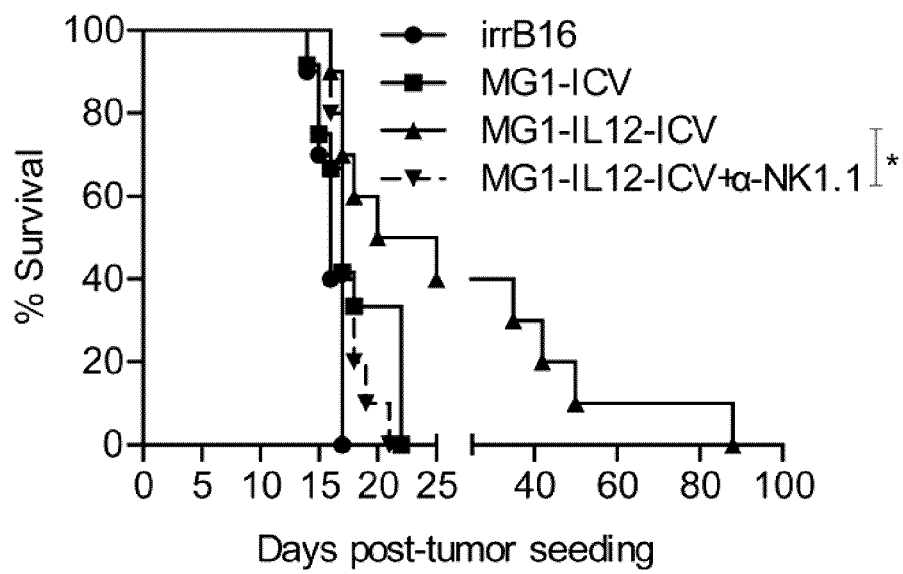

FIG. 18 demonstrates that the increased survival of tumour-bearing mice following vaccination with MG1-IL12 ICV is NK cell dependent as this effect is abrogated by NK cell depletion using an anti-NK1.1 antibody.

Figure 19:
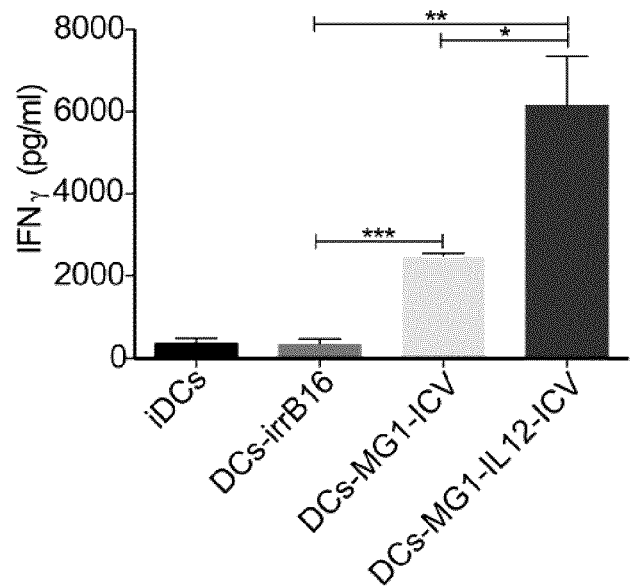

FIG. 19 shows increased IFNγ secretion by splenocytes isolated from naïve mice and co-cultured with isolated Dendritic Cells (DCs) that have been stimulated with MG1-IL12 ICV.

Figure 20:
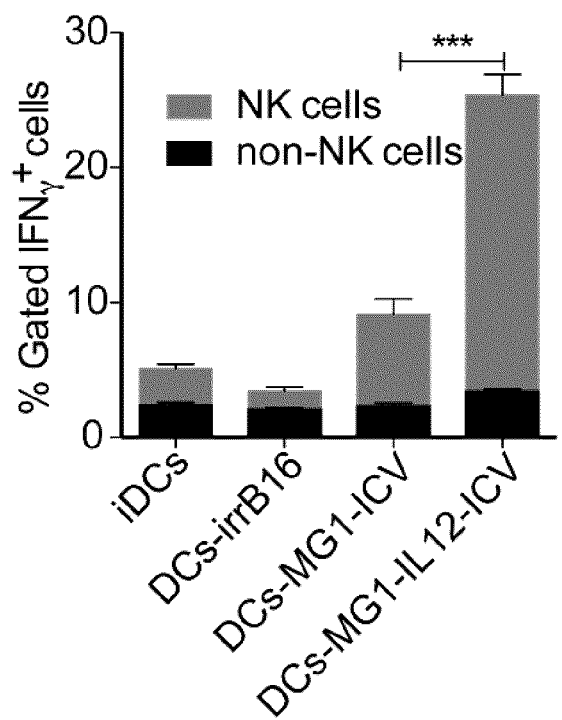

FIG. 20 shows that the increase in IFNγ secretion by splenocytes isolated from naïve mice and co-cultured with isolated DCs that have been stimulated with MG1-IL12 ICV is primarily due to the NK cell population.

Figure 21:
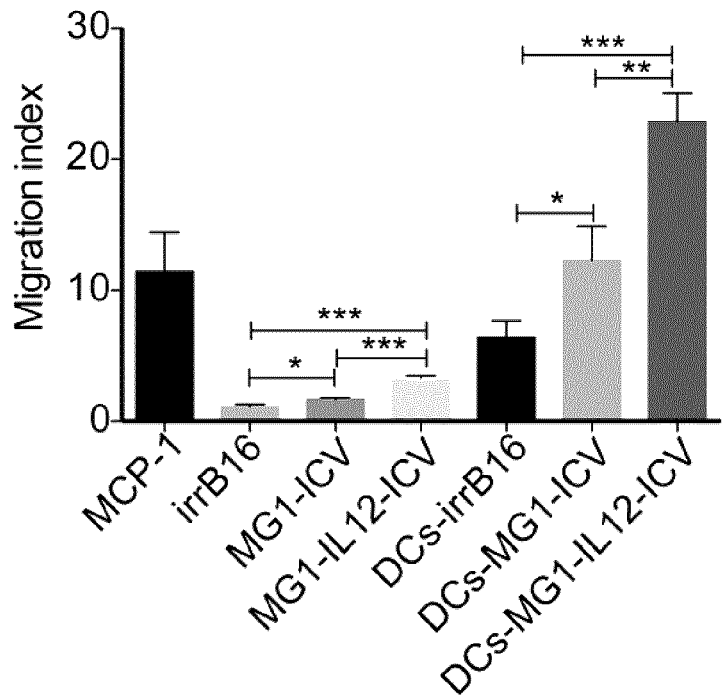

FIG. 21 shows the results of a chemotaxis assay demonstrating an increase in migration of isolated naïve NK cells into cell free media conditioned with isolated DCs that have been stimulated with MG1-IL12 ICV.

Figure 22:
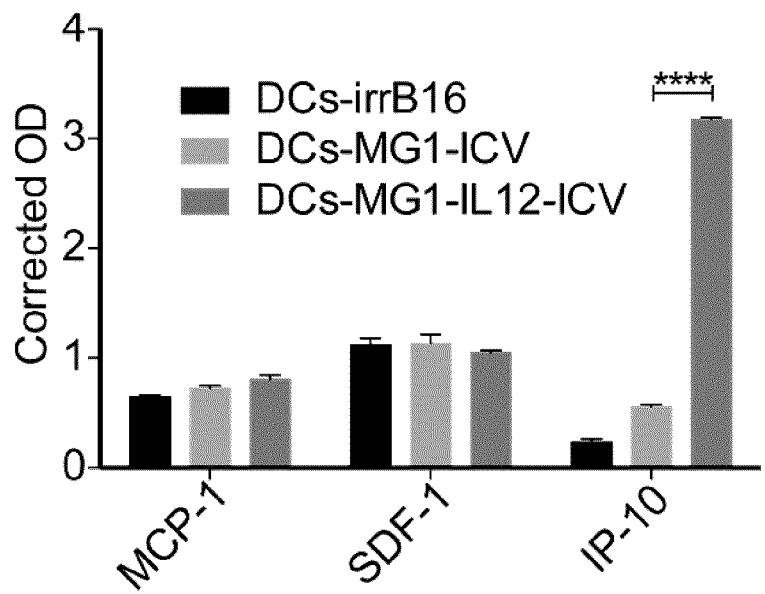

FIG. 22 demonstrates that IP-10 chemokine is released into culture media following co-culture of DCs stimulated with MG1-IL12 ICV.

Figure 23:
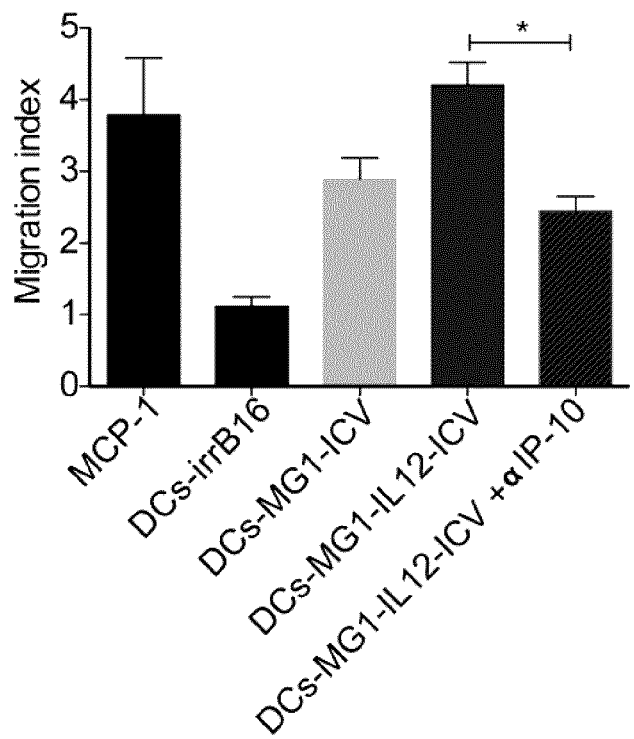

FIG. 23 demonstrates that neutralization of IP-10 with IP-10 neutralizing antibodies abrogates NK cell chemotaxis induced in conditioned media with DCs stimulated by MG1-IL12 ICV.

Figure 24:
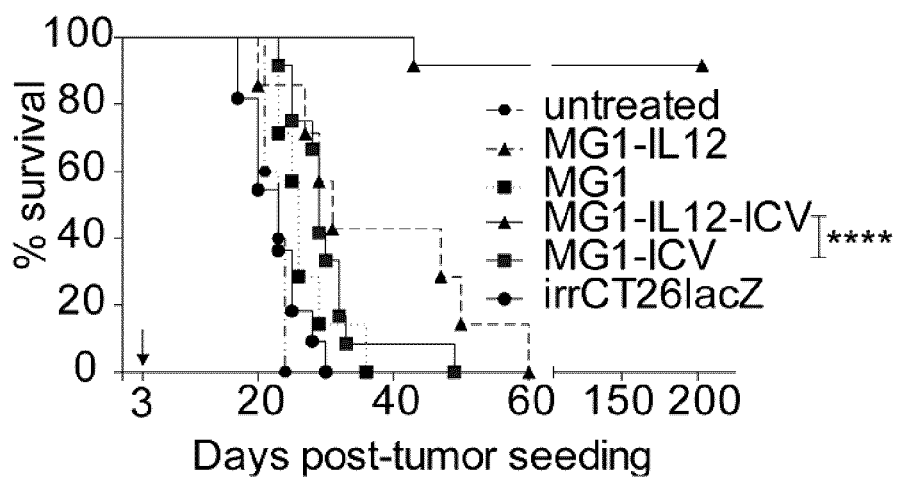

FIG. 24 illustrates the beneficial effect on survival of mice after initial tumour seeding and following vaccination with MG1-IL12 ICV versus MG1 ICV or treatment with either virus MG1 or recombinant virus MG1-IL12 alone.

Figure 25:
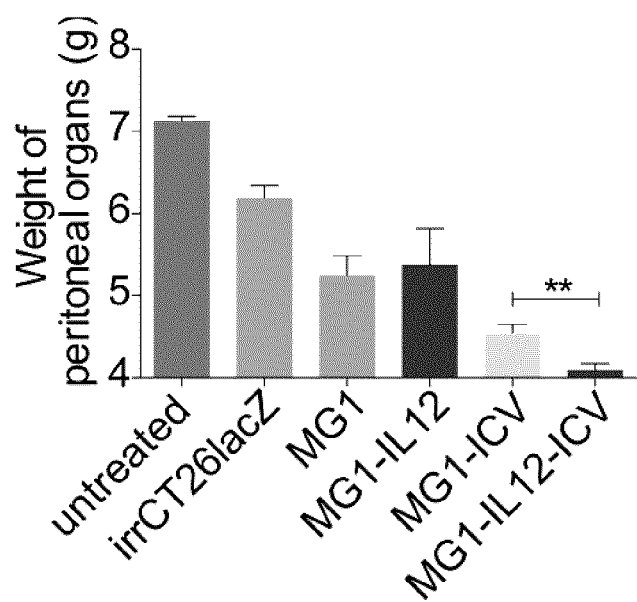

FIG. 25 demonstrates that the increased survival following vaccination with MG1-IL12 is accompanied by a corresponding decrease in the gross weight of peritoneal organs (including associated tumour burden).

Figure 26:
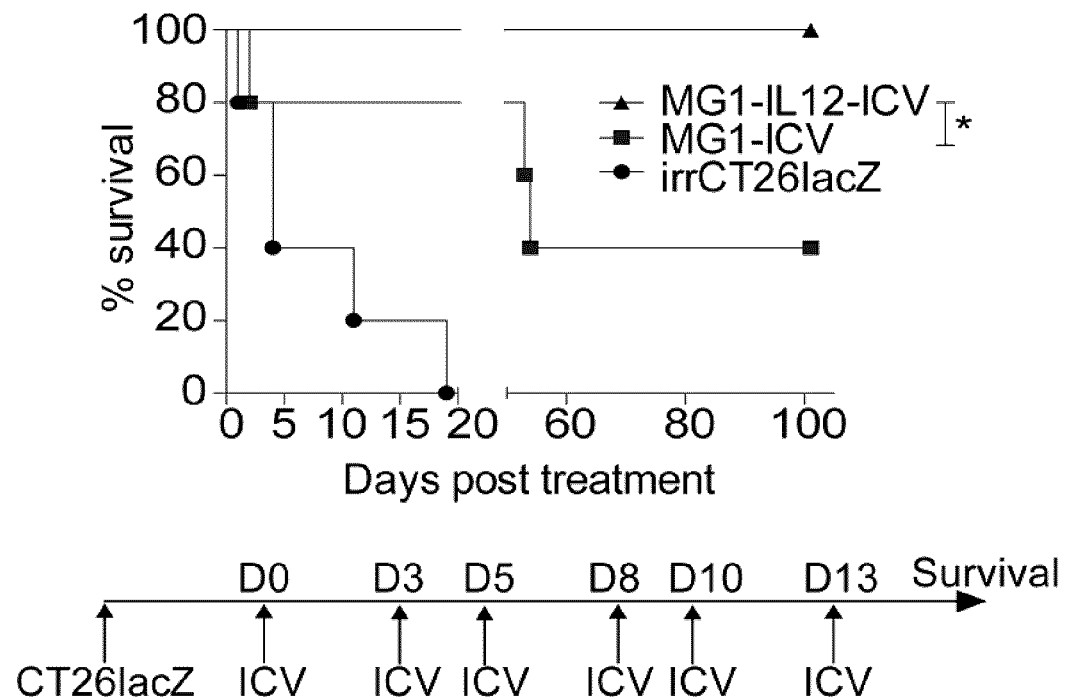

FIG. 26 illustrates the beneficial effect on survival of mice with large advanced tumours vaccinated with MG1-IL12 ICV biweekly for a period of three weeks.

Figure 27:
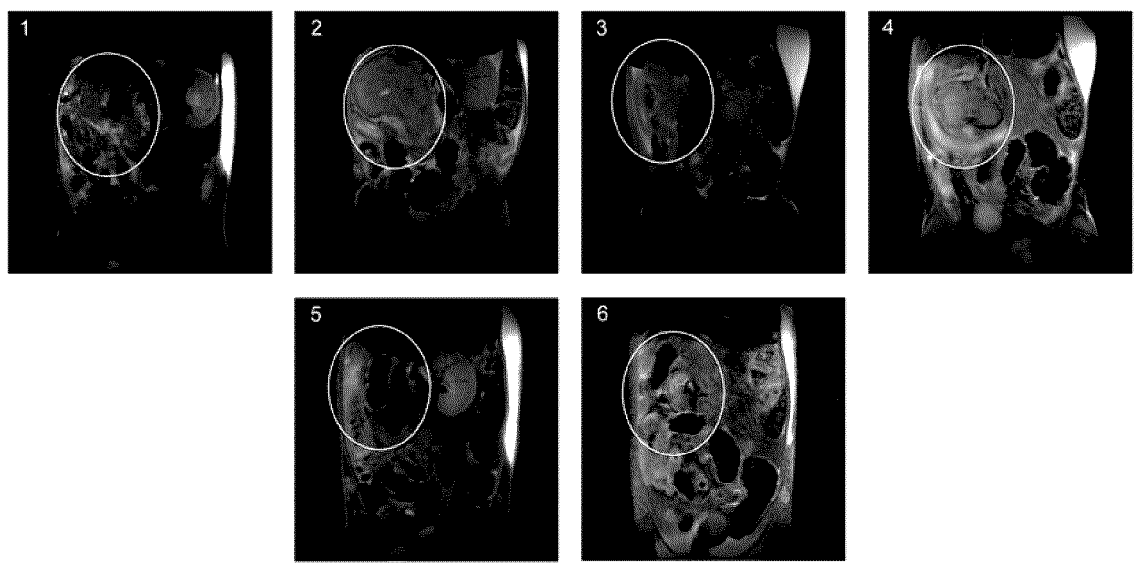

FIG. 27 shows MRI scans for one representative mouse vaccinated with MG1-IL12 ICV demonstrating shrinking tumour burden overtime.

Figure 28:
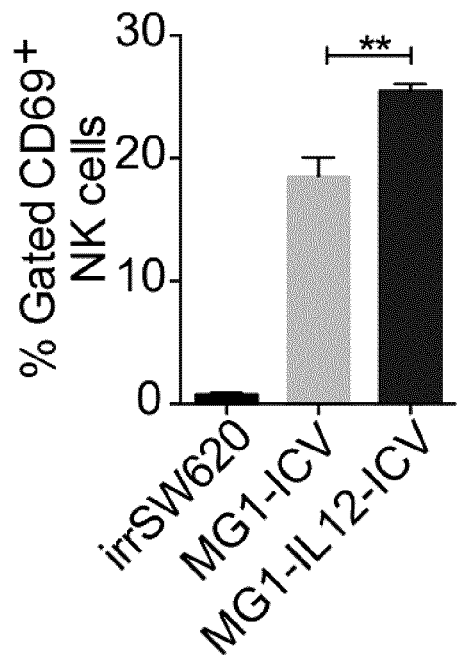

FIG. 28 shows the increased activation of human NK cells in PBMCs cultured with SW620 cells infected with MG1-IL12 ICV.

Figure 29:
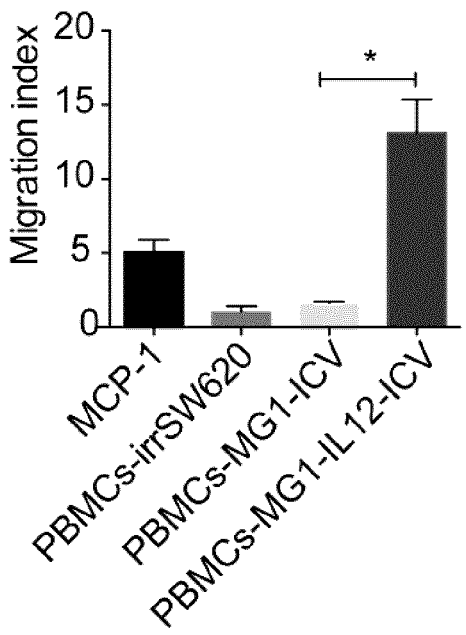

FIG. 29 demonstrates that the stimulatory effects of cell free conditioned media prepared from PBMCs cultured with SW620 cells infected with MG1-IL12 ICV elicit increased migration in human NK cells.

Figure 30:
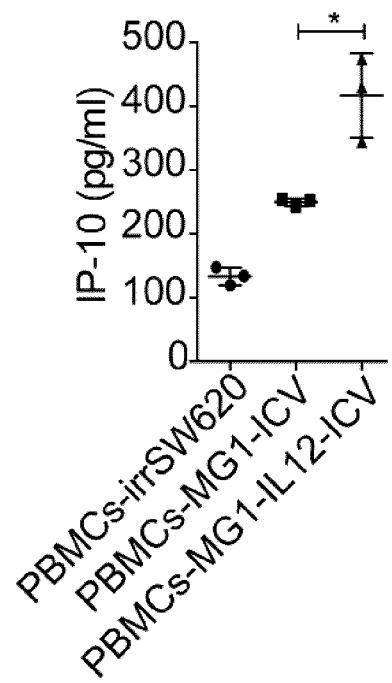

FIG. 30 shows increased IP-10 chemokine production following co-culture of human PBMCs with SW620 cells infected with MG1-IL12 ICV.

Figure 31:
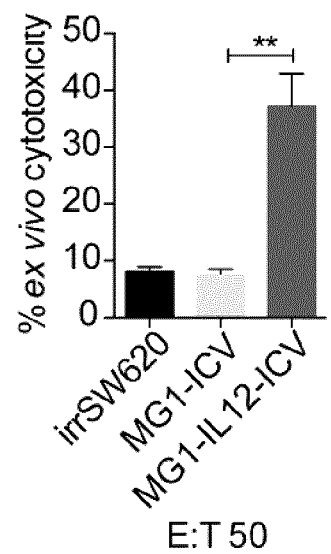

FIG. 31 shows an enhanced ex vivo cytotoxicity of isolated NK cells from human cancer patients that were cultured with SW620 cells infected with MV1-IL12 ICV at an effector:target ratio of 50:1.

Figure 32:
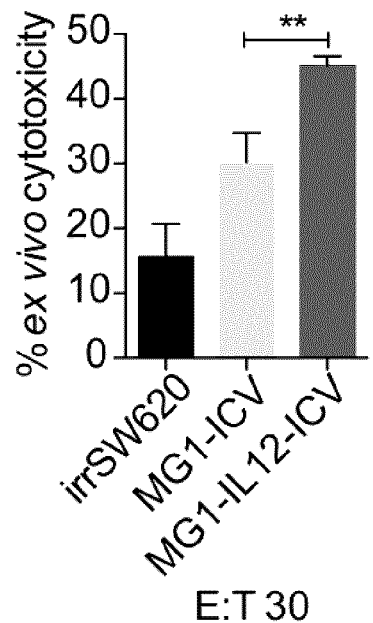

FIG. 32 shows an enhanced ex vivo cytotoxicity of isolated NK cells from human cancer patients that were cultured with SW620 cells infected with MG1-IL12 ICV at an effector:target ratio of 30:1.

Figure 33:
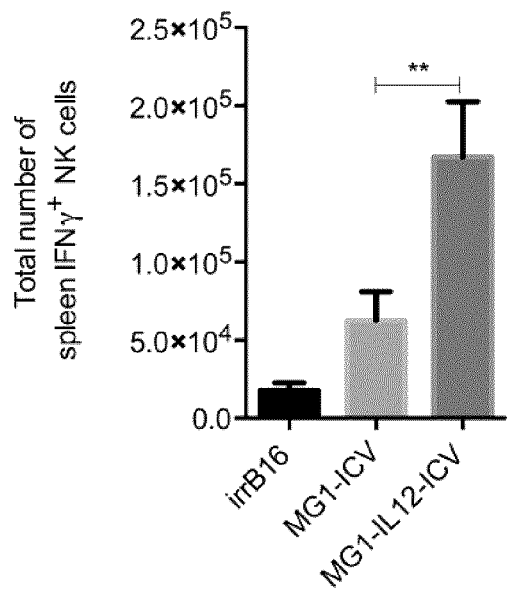

FIG. 33 shows an increase in the total number of NK1.1+ IFNγ+ cells in the spleen of tumour naïve mice after systemic IV treatment with MG1-IL12 ICV.

Figure 34:
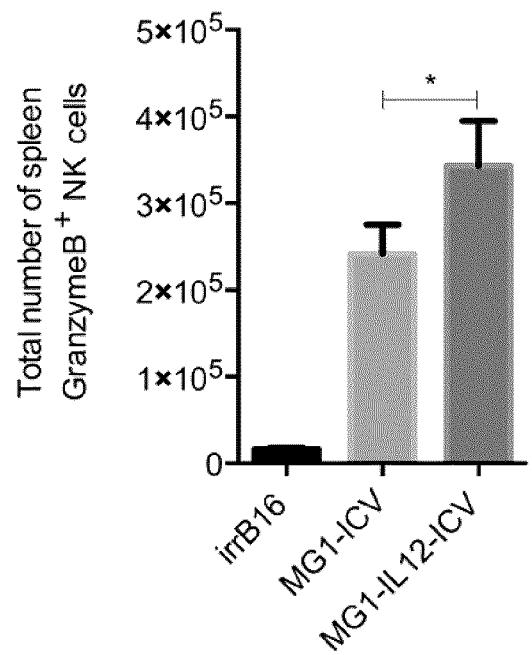

FIG. 34 shows an increase in the total number of NK1.1+ GramzymeB+ cells in the spleen of tumour naïve mice after systemic IV treatment with MG1-IL12 ICV.

Figure 35:
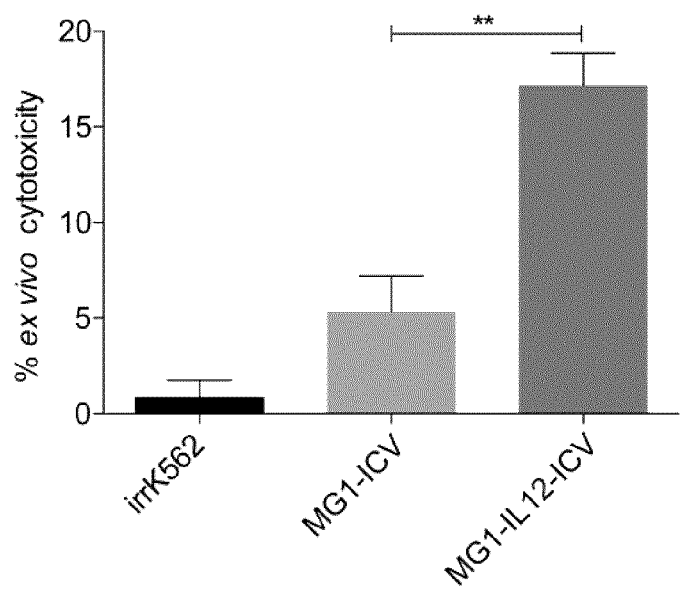

FIG. 35 shows results of an ex vivo chromium release cytotoxicity assay using an individual healthy patient PBMCs cultured with K562 cells infected with MG1-IL12.

Figure 36:
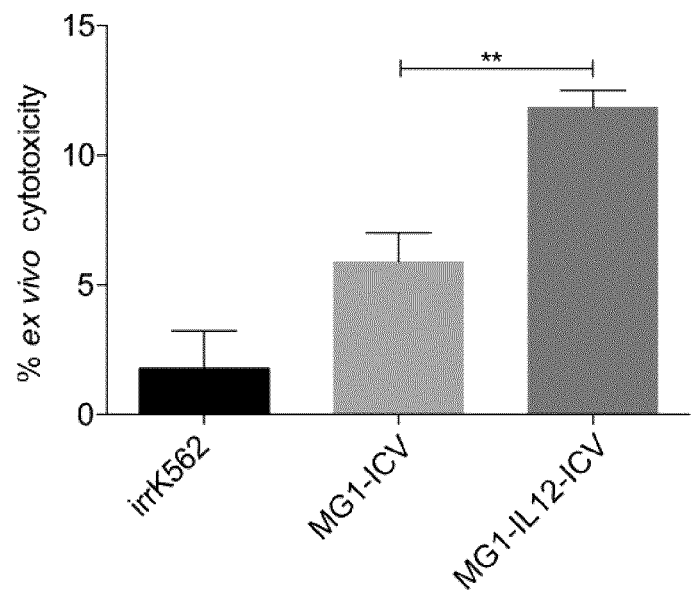

FIG. 36 shows results of an ex vivo chromium release cytotoxicity assay using an individual healthy patient PBMCs cultured with K562 cells infected with MG1-IL12.

Figure 37:
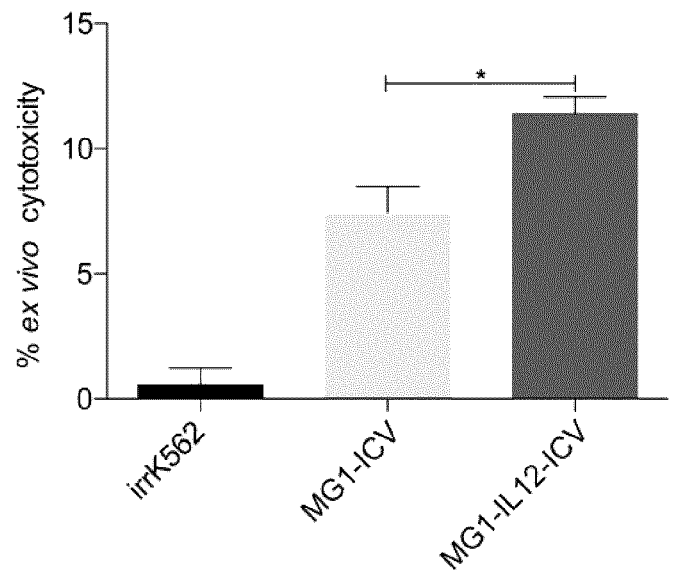

FIG. 37 shows results of an ex vivo chromium release cytotoxicity assay using an individual cancer patient PBMCs cultured with K562 cells infected with MG1-IL12.

Figure 38:
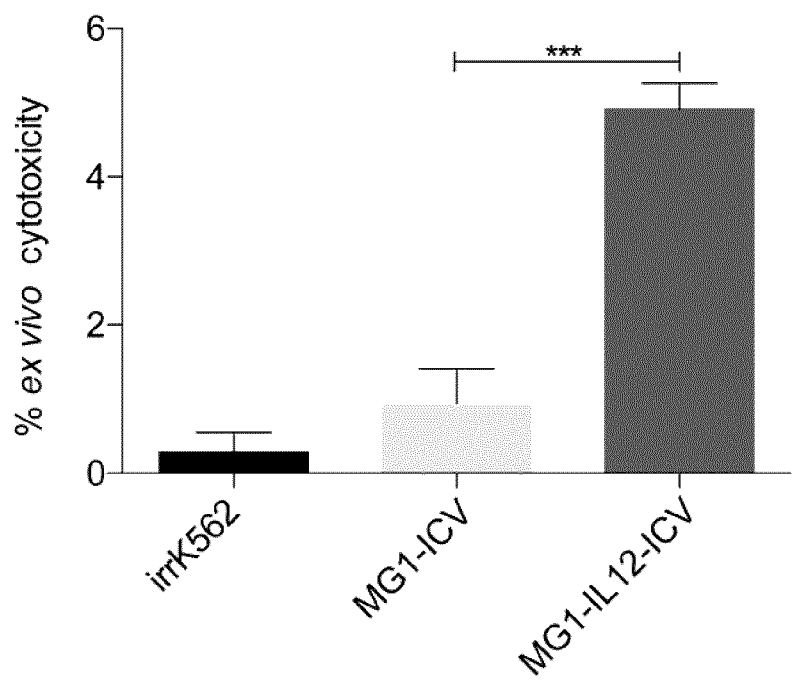

FIG. 38 shows results of an ex vivo chromium release cytotoxicity assay using an individual cancer patient PBMCs cultured with K562 cells infected with MG1-IL12.

Figure 39:
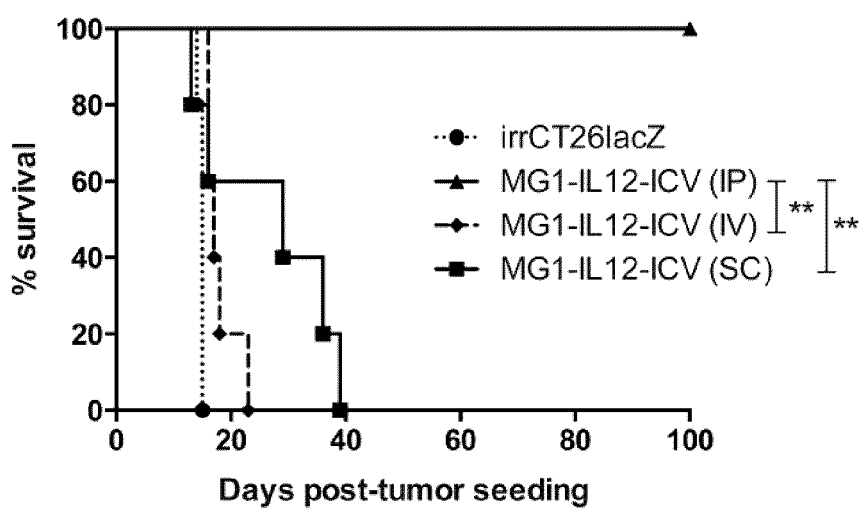

FIG. 39 shows the differential efficacy of using different routes of MG1-IL12 ICV administration in BALB/c mice following tumour seeding.

Figure 40:
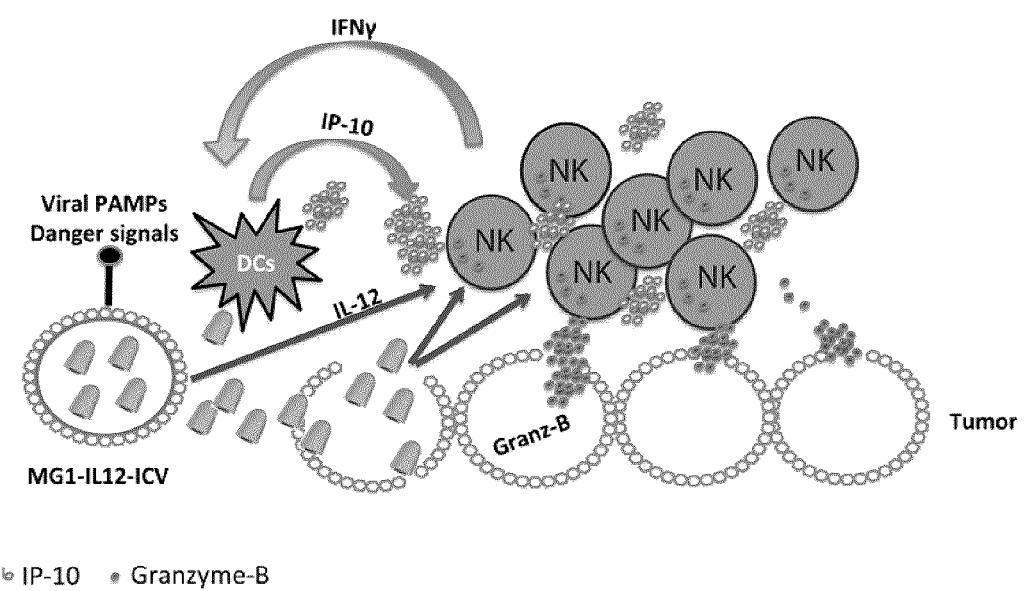

FIG. 40 illustrates a proposed model for the mechanism of NK cell recruitment and activation following vaccination with MG1-IL12 ICV.

DETAILED DESCRIPTION

Generally, the present disclosure provides: a Maraba virus whose genome includes a transgene sequence that encodes the cytokine IL12; an infected cell vaccine (ICV) where autologous tumour cells from a patient are infected ex vivo with an oncolytic recombinant rhabdovirus expressing IL12; a method to treat a cancer through administration of the Maraba virus or the infected cell vaccine; and use of the Maraba virus or the infected cell vaccine for treating a cancer. Without wishing to be bound by theory, the authors of the present disclosure believe that expression of the IL12 may enhance the anti-tumour immune response of the administered oncolytic virus.

Peritoneal carcinomatosis (PC) is one of the most common and problematic sites of metastases for abdominal malignancies, including gastrointestinal and ovarian cancers (7). It is a common cancer metastases that is associated with a significantly reduced quality of life, median survival rate and poor prognosis that requires new treatment options. PC poses challenges to the use of traditional chemotherapy, which cannot be used for patients who develop complications such as bowel obstruction (8). Another challenge in treating PC is the difficulty in delivering a therapeutic agent. Another obstacle to effective therapy is the toxicity and short half-life of immunomodulating agents used systemically or delivered directly to the target site.

One aspect of the present disclosure may overcome one or more of these challenges by enhancing the anti tumour immune response of an oncolytic virus. By way of example, in one particular embodiment, the patients' tumour cells are infected ex vivo with an oncolytic rhabdovirus expressing the cytokine IL12. These infected cells are then re-administered to the patient as an Infected Cell Vaccine (ICV). Without wishing to be bound by theory, the authors of the present disclosure believe that the infected tumour cells provide an immunostimulatory environment that is supplemented by the production of IL12. Expression of IL12 in situ reduces the half-life and/or toxicity drawbacks associated with high dose administration of IL12. The authors of the present disclosure believe that expression of the IL12 acts to recruit and stimulate NK cells to the tumour site, and reduce the size of the tumour. The activation of NK cells, the adaptive arm of the immune response, may confer a long-term memory and thereby reduce the possibility that the tumour will return.

Material and Methods:

Cell Lines and Mice:

Murine CT26 colon carcinoma, murine B16F10 F10 melanoma, human SW620 colorectal adenocarcinoma, human HCT15 colorectal adenocarcinoma, human A549 lung carcinoma, murine YAC-1 lymphoma, human K562 leukemic cell lines (all from American Type Tissue Collection) were propagated in Dulbecco's modified Eagle's medium (Hyclone) for the adherent cell lines, or Roswell Park Memorial Institutes Media (Hyclone) for non-adherent cell lines supplemented with 10% fetal calf serum (Cansera, Etobicoke, Ontario, Canada). Rauscher murine leukemia virus-induced T-cell lymphoma (RMA) and RMA-S (MHC-deficient variant of RMA) were obtained from Dr. A. Veillette (Institut de Recherches Clinique, Montreal, Quebec, Canada). Female Balb/C and C57BL/6 mice 6- to 8 weeks old were purchased from Charles River Laboratories (Wilmington, Mass.). Animals were housed in pathogen-free conditions and all experiments were conducted with the approval of the University of Ottawa Animal Care and Veterinary Service.

MG1-IL12 construction:

Murine IL12 was PCR amplified from pORF-mIL-12 (IL-12elasti(p35::p40)) (InvivoGen, San Diego, Calif., USA) to add MluI (5') and (3') cloning sites to facilitate cloning into Maraba MG1 (9). The recombinant MG1-IL12 virus was rescued as described previously (10). Briefly, A549 were infected with vaccinia virus expressing T7 polymerase and subsequently transfected using Lipofectamine 2000 (Invitrogen, Burlington, ON, Canada) with 2 mg of MG1-IL-12 DNA plasmid together with pCI-Neo plasmids encoding for Maraba N, P and L (1, 1.25, 0.25 mg, respectively). The rescued virus was passaged on SNB19 cells, then plaque purified, amplified and titered on Vero cells.

Viability Assays:

B16lacZ, CT26lacZ, SW620 and HCT15 cell lines were seeded into 96-well plates ($2 \times 10^4$ cells/well). 24 hours later, cells were infected with MG1 or MG1-IL12 viruses at Multiplicity of Infection (MOI) of 0.001-10 pfu/cell. Alamar Blue (Sigma-Aldrich, St Louis, Mo.) was added following 48 hours of incubation to a final concentration of 20 µg/ml. The absorbance was read at a wavelength of 570 nm after 6-hour incubation.

Antibodies and FACS Analysis:

For splenic and lung lymphocyte population analyses, organs were harvested from mice and red blood cells lysed using ammonium chloride-potassium lysis (ACK) buffer. The following monoclonal antibodies were used: anti-TCR-b (H57-597), anti-NK1.1 (PK136), both from eBiosciences. Spleen and lung NK cell IFN-γ and Granzyme B secretion were analysed following a 1 hour GolgiPlug (BD Biosciences) incubation using: anti-CD3 (17A2), anti-NK1.1 (PK136), anti-IFN-γ (XMG1.2) and anti-Granzyme B (16G6) all from BD Biosciences. The monoclonal antibodies were used for human NK cell migration and activation are; anti-CD56 (HCD56) from Biolegend, anti-CD3 (UCHT1) and anti-CD69 (FN50) both are from eBiosciences. Fluorescence-activated cell sorting (FACS) acquisitions were conducted on a CyAn-ADP using Summit software (Beckman Coulter, Mississauga, Canada) and data were analyzed with Kaluza software (Beckman Coulter).

Ex Vivo Splenocytes Cytotoxicity Assay

The $^{51}$Cr-release assay was performed as previously described (11). Briefly, splenocytes were harvested from treated and control mice two days after treatment. ACK buffer treated splenocytes were resuspended and mixed with chromium labelled YAC-1 cells at specified effector-to-target (E:T) ratios.

In Vivo Tumour Rejection Assay

The in vivo rejection assay was performed as described previously (11). Briefly, RMA and RMA-S were labeled with 5 and 0.5 mmol/L CFSE, respectively. $1 \times 10^6$ cells containing a 1:1 mixture of each cell type was injected i.p. into C57BL/6 mice 24 hrs following ICV treatment. Peritoneal cells were collected the following day (24 hr) by washing the peritoneum with 5 mL of PBS containing 2 mmol/L EDTA. Collected cells were analysed by flow cytometry for the presence of CFSE-labeling.

Virus Infection of B16F10 Cells and Co-Culture with Bone Marrow-Derived DCs for Chemotaxis and Chemokines Analysis B16F10 cells infected with MG1 or MG1-IL12 (MOI=0.1 pfu/cell) were harvested 18 hrs after infection and cultured with bone marrow-derived dendritic cells (DCs) described elsewhere at a 3:1 ratio in DC medium (1% FBS) (complete RPMI supplemented with 1× of 2-Mercapoethanol (cat #21985-023, Gibco, life technologies) in 96-wells plates (12). Media was collected after 24 hours and stored at −80° C. until further analysis.

Cytokine and Chemokine Analyses

Murine IFNγ from DCs co-culture supernatant were detected by FlowCytomix (eBioscience) kits as per manufacturer's instructions. For lungs IL12 and IFNγ expression, lungs from C57Bl/6 mice treated with irrB16, MG1 ICV or MG1-IL12 ICV at $5 \times 10^5$ cells/100 ul/mouse i.v., were resected and homogenized in 1 ml PBS 24-hours after treatment. Murine MCP-1, SDF-1 and IP-10 chemokines were assayed 18 hours post ICV treatment from the peritoneal fluids of C57Bl/6 mice (in vivo) or from tissue culture supernatant using ELISArray kits (SABiosciences) as per manufacturers instructions.

Murine Transwell Chemotaxis Assay

Tissue culture supernatants for assessment of chemokines or chemotaxis assay were generated in DC media. Chemotaxis of NK cells was assessed using a Transwell system as described previously (13). Briefly, 500 ul of conditioned media from DC cultures was added to the lower chamber of Transwell plates with 5-um pores (Costar, Corning). $3 \times 10^5$ of DX5$^+$ sorted NK cells were added to the upper chamber, and plates were incubated for 3 hours at 37° C. Cells in the lower chambers were harvested, stained with trypan blue and counted. A migration percentage was calculated as (total number NK cells in bottom chamber/total number NK cell input)×100. To calculate NK cell index: (NK cell migration percentage/NK cell migration percentage from media alone group).

Human Transwell Chemotaxis Assay

Conditioned media were generated in DC media through direct ICV-PBMCs co-culture at 3:1 ratio for 18 hours. $1\times10^6$ of PBMCs were added to the upper chamber, and plates were incubated for 3 hours at 37° C. Cells in the lower chambers were harvested, stained with anti-CD56 (HCD56) and anti-CD3 (UCHT1) and quantified by FACS. A migration percentage was calculated as (total number NK cells in bottom chamber/total number NK cell input)×100. To calculate NK cell index: (NK cell migration percentage/NK cell migration percentage from media alone group).

DC-MG1-IL-12-ICV/Splenocytes Co-Cultures

DC-MG1-IL-12-ICV were isolated by MACS CD11c+ selection (Miltenyi Biotec) and co-cultured with naïve splenocytes at 1:5 ratio in DC medium, at $2\times10^5$ splenocytes/well in 96-well plate format. Twenty-four hours later, cell-free supernatant was stored at −80° C. for measurement of IFNγ. Intracellular IFNγ staining on splenocytes by intracellular FACS was also performed as described above.

Mouse Models:

Therapeutic Treatment Model.

CT26 and B16F10 Peritoneal carcinomatosis in BALB/c and C57Bl/6 mice, respectively were treated with $1\times10^4$ ICV on day 3 after seeding $5\times10^5$ tumour cells intraperitonealy. For the CT26 bulky tumour model, $5\times10^5$ tumour cells were seeded within the peritoneum and the treatment regimen of six doses of ICV was initiated following Magnetic Resonance (MR) scan confirmation of a tumour with a size of >3 mm. Animals were sedated with isoflurane gas and MR scanning was performed with a 7 Tesla GE/Agilent MR 901 (GE Healthcare, Chicago, USA). For each mouse, three MR pulse sequences were used: one localizer and two fast spin echo (FSE) sequences in the coronal and axial planes. The parameters for the FSE sequences were: echo train length 8, bandwidth=16 kHz, echo time=42 ms, repetition time=1500 ms, field of view=35 mm, matrix 256×256, slice thickness=1 mm. The total MR scan time per mouse was approximately 15 minutes. Follow-up MR scans were performed one week, six weeks and thirteen weeks post-treatment start using the same MR scan parameters.

Prophylactic Treatment Model.

C57Bl/6 mice were vaccinated with single dose of $1\times10^3$ irrB16, MG1 ICV or MG1-IL-12-ICV ip The following day, mice were challenged with $3\times10^5$ B16F10-LacZ cells IV, sacrificed at 4 days after tumours cells injection followed by staining and quantification of lung metastases with X-gal (Bioshop, Burlington, Canada) as described previously (14). The total number of lung surface metastases was determined on all lung lobes using a stereomicroscope (Leica Microsystems, Concord, Canada).

Statistical Analysis

All statistical analyses were determined using GraphPad Prism 6.0 software. Statistical significance was determined by the Student t test with a cut off P=0.05. Data are presented as ±SD.

Characterization of an MG1 Oncolytic Virus Encoding Murine IL12 (MG1-IL12)

Figure 1:
Figure 2:
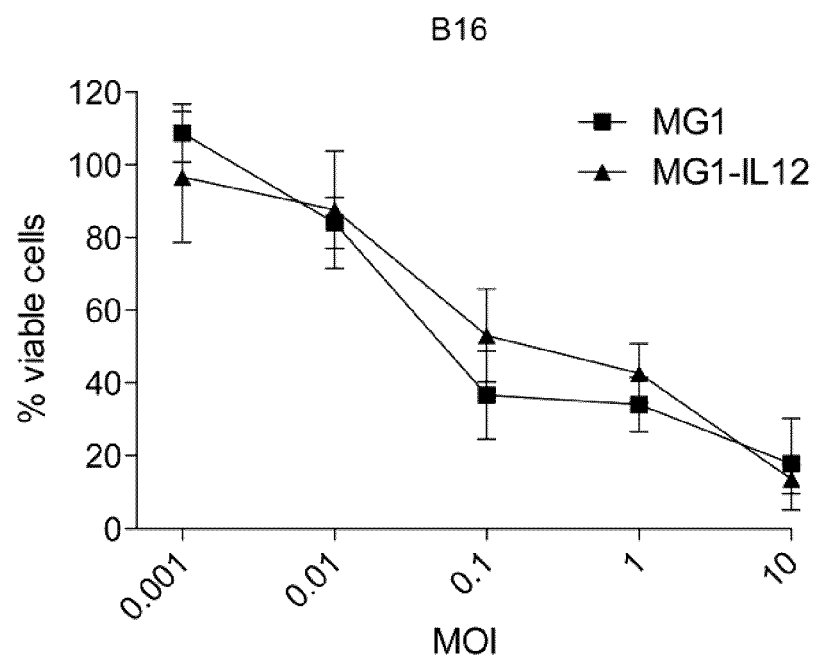
Figure 3:
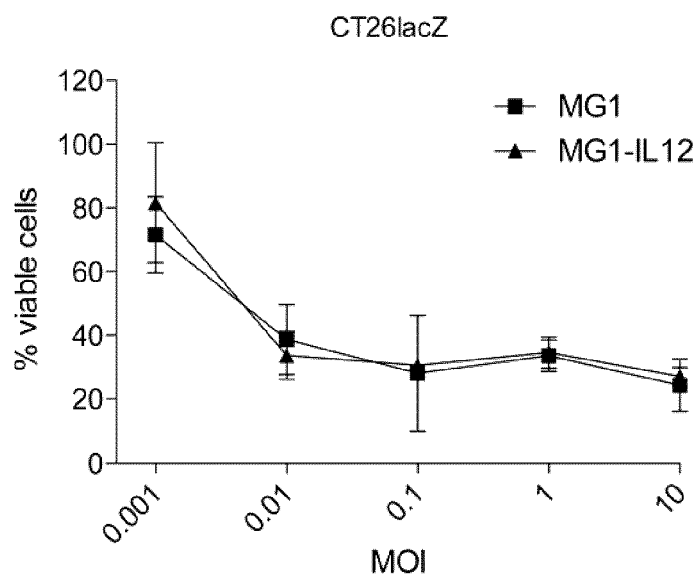
Figure 4:
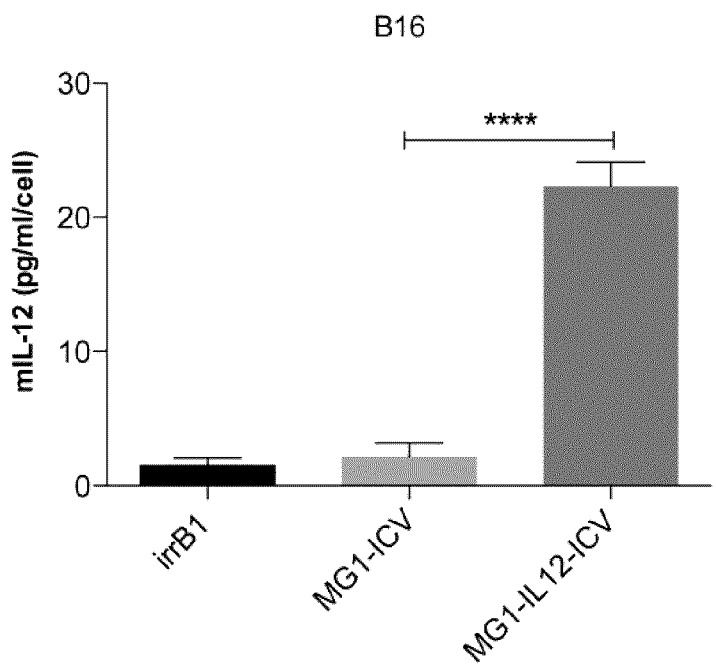
Figure 5:
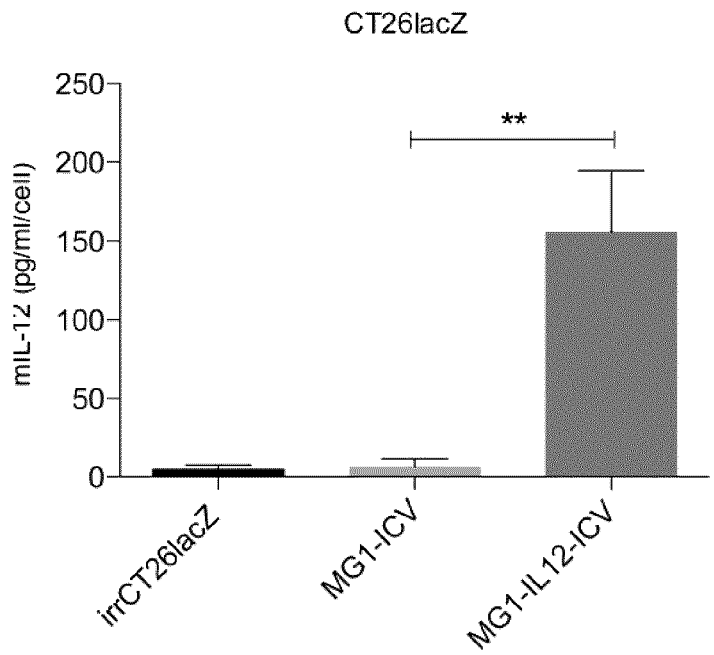

A murine IL12 transgene (p70), which is composed of p35 and p40 subunits, was incorporated into the backbone of the oncolytic Maraba virus variant MG1 to create MG1-IL-12 (FIG. 1). This replication competent oncolytic virus was found to infect both murine and human tumour cell lines with an efficiency comparable to parental MG1 and expression of IL12 did not negatively impact viral replication or spreading (FIGS. 2 and 3). Furthermore, IL12 was detected in the culture media of B16F10 (22 pg/cell) and CT26 (180 pg/cell) cells infected with MG1-IL12 (FIGS. 4 and 5). Together these results demonstrate that MG1-IL-12 can successfully infect murine tumour cells resulting in viral replication and IL-12 secretion, resulting in an MG1-IL12 infected cell vaccine (ICV).

Examples

MG1-IL12 ICV Enhances NK Cell-Mediated Tumour Rejection.

Figure 6:
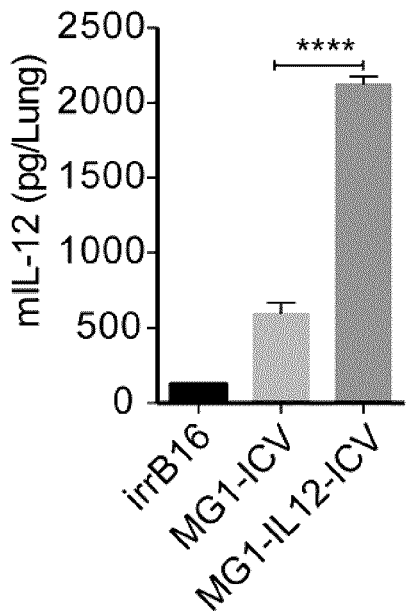
Figure 7:
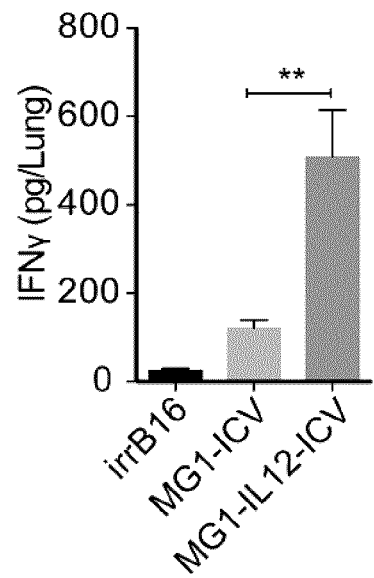
Figure 8:
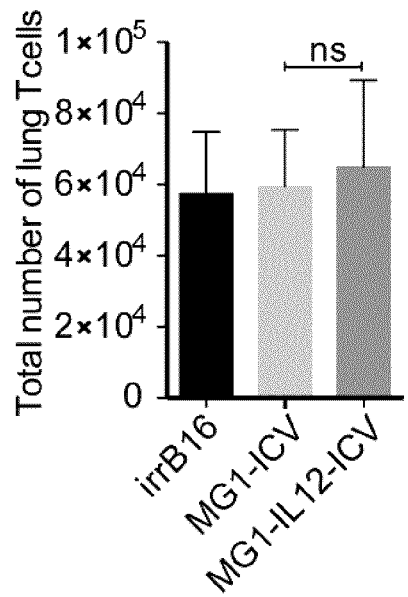
Figure 9:
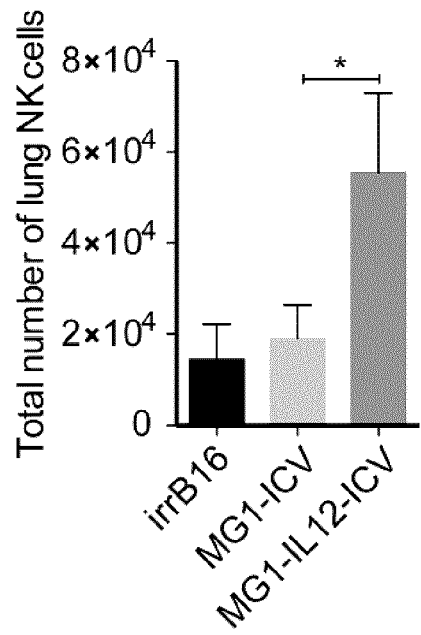
Figure 10:
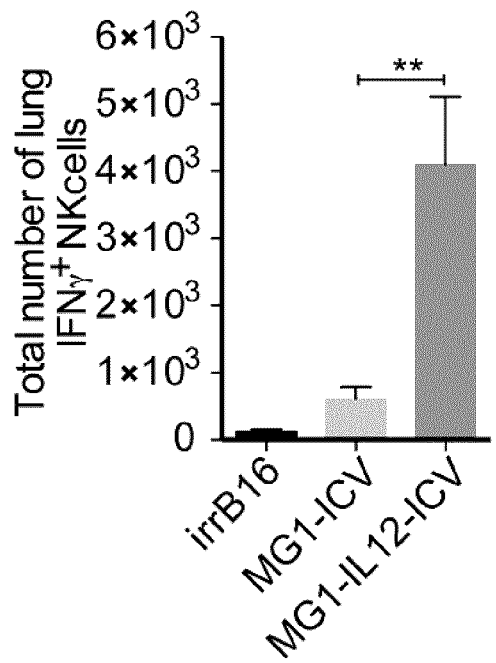
Figure 11:
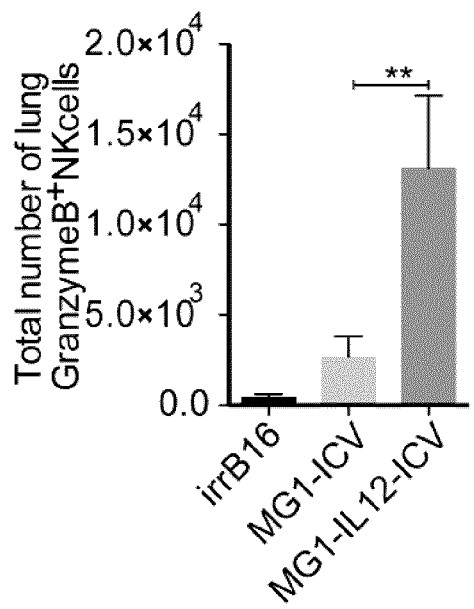
Figure 12:
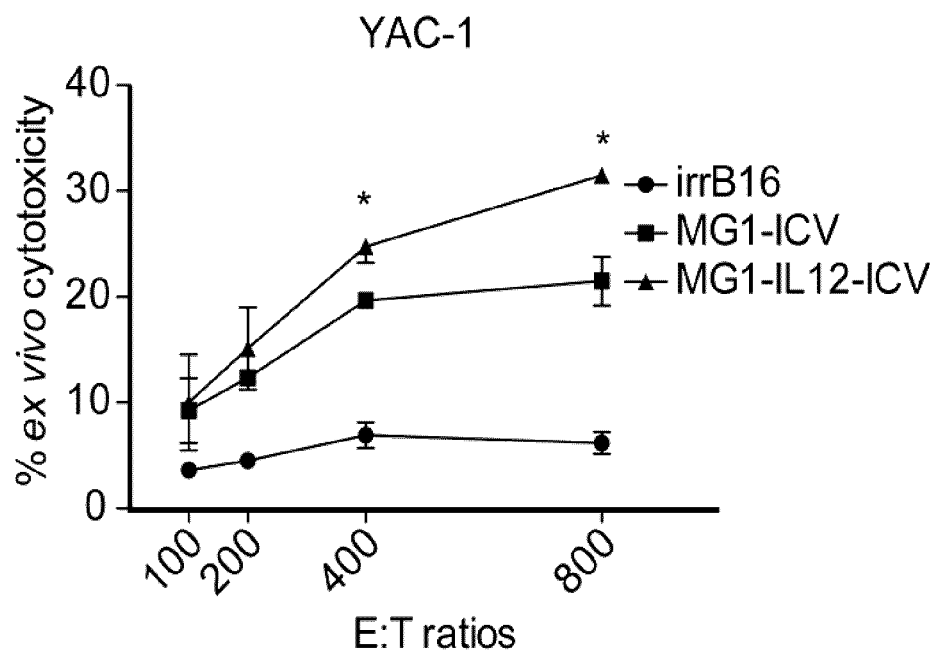
FIG. 12 shows results of an ex vivo chromium release cytotoxicity assay of splenocytes isolated from tumour naïve mice following treatment with MG1-IL12 ICV, demonstrating increased killing of target YAC1 cells.
Figure 13:
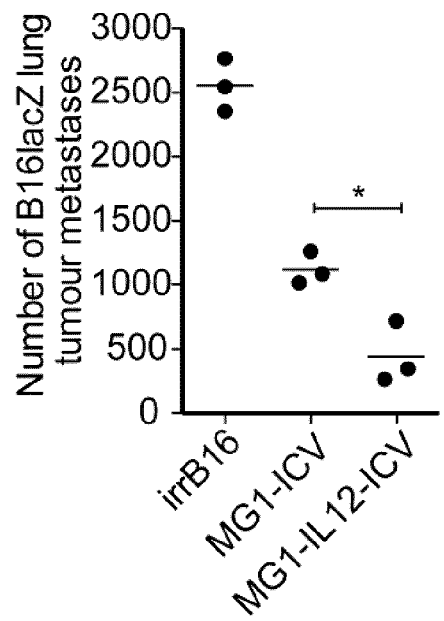
FIG. 13 shows a decrease in B16F10 lung metastasis following IV administration of MG1-IL12 ICV to mice compared to administration of MG1 ICV without IL12, and to uninfected B16F10 cells.

The authors of the present disclosure have previously demonstrated that infecting autologous tumor cells ex vivo with oncolytic viruses can elicit a robust immune response against established, non-permissive, tumors in vivo (15). To determine whether MG1 and MG1-IL12 could similarly induce an immune response when used as an ICV, the authors intravenously (i.v.) injected $5\times10^5$ γ-irradiated B16F10 cells either mock infected or infected with MG1 or MG1-IL12. The authors have previously shown that i.v. administration of ICVs is associated with a rapid and dose-dependent accumulation of injected cells which persist in the lung for up to 1 day in tumor free animals (16). Following ICV delivery, significantly higher levels of IL12 were detected in lung homogenates from mice receiving MG1-IL12 ICV in comparison to animals receiving cells alone or MG1 ICV (FIG. 6, t=24 hr). To determine whether the increased concentrations of IL12 had any functional effect, the levels of the IL12 responsive cytokine IFNγ were measured. In agreement with the increase in IL12, levels of IFNγ were also elevated in the lungs of mice treated with MG1-IL12 ICV compared to mice receiving MG1 ICV or irradiated cells (FIG. 7). Since IL12 targets both NK and T cells to promote IFNγ secretion (17), the authors next sought to determine which cell types were responding to treatment with our MG1-IL12 ICV. Interestingly, vaccination with MG1-IL12 ICV was not found to impact the total number of T cells in the lung, however, a 3-fold increase in the total number of NK cells present in the lung was observed suggesting that MG1-IL12 ICV enhances NK cell recruitment (FIGS. 8 and 9). In addition, the total number of IFNγ and granzyme B positive NK cells was increased approximately 7 and 4-fold respectively following injection of MG1-IL12 ICV indicating an increase in NK cell activation (FIGS. 10 and 11). To further examine the effect, the cytotoxic activity of NK cells against YAC-1 target cells was measured ex vivo and it was observed that splenocytes isolated from MG1-IL12 ICV treated mice exhibited a significantly higher level of YAC-1 killing (FIG. 12). These data supported a role for MG1-IL12 ICV in promoting NK cell recruitment to the site of delivery and a concomitant systemic activation of splenic NK cells (FIGS. 33 and 34). In order to determine if this effect translated into improved tumour clearance, B16F10 lung metastases were treated with either irradiated cells, MG1-IL12 ICV, or MG1 ICV alone by i.v. delivery (FIG. 13). Systemic delivery of MG1-IL12 ICV was sufficient to significantly attenuate the number of detectable lung metastasis in comparison to treatment with MG1 ICV or irradiated cells. These results suggest that MG1-IL12 ICV can stimulate NK cell recruitment and effector function to significantly improve the antitumour efficacy of the infected cell vaccines.

MG1-IL12 ICV Enhances NK Cell Activation and Improves Survival in a Model of Peritoneal Carcinomatosis.

The initial findings suggest that the improved anti-tumor response elicited by MG1-IL12 ICV in comparison to MG1 ICV are in part due to potent chemotactic properties of IL12 which contribute to the enhanced recruitment of cytotoxic NK cells to the site of delivery (FIGS. 9,10 and 11).

Figure 14:
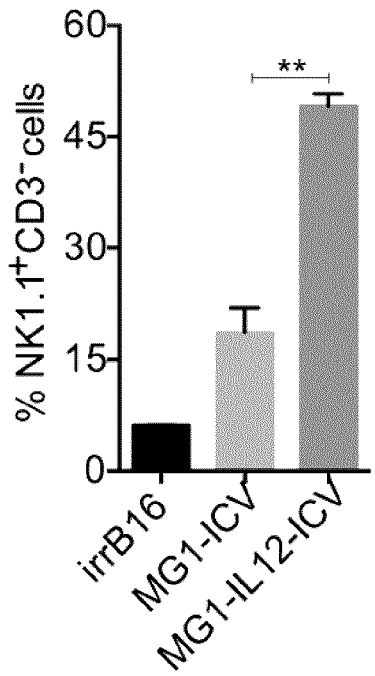
FIG. 14 shows an increase in recruitment of NK (NK1.1− CD3−) cells in the peritoneal cavity of mice vaccinated with MG1-IL12 ICV.
Figure 15:
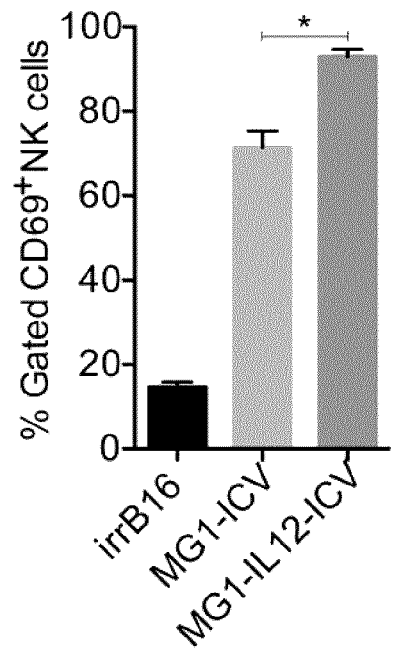
FIG. 15 shows that the accumulating NK (NK1.1− CD3−) cells in the peritoneal cavity of mice vaccinated with MG1-IL12 ICV are activated as measured by CD69 staining.
Figure 16:
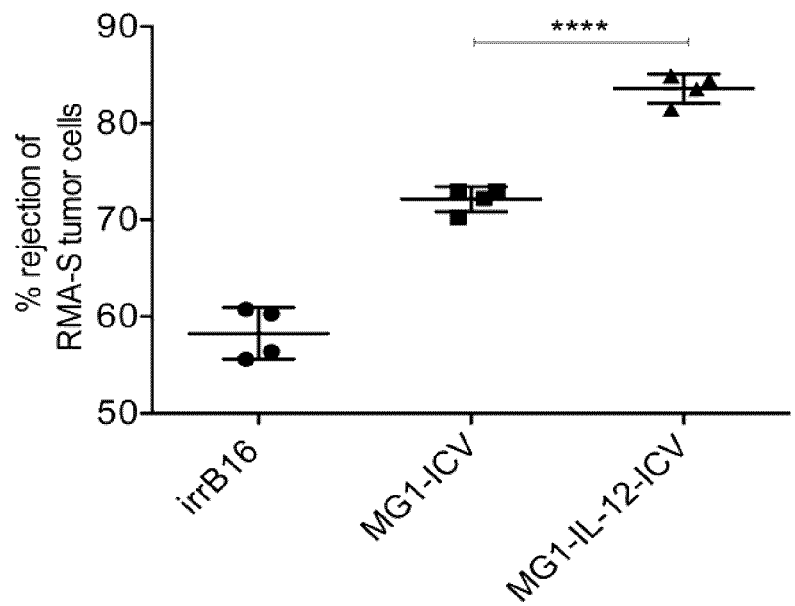
FIG. 16 shows that mice vaccinated with MG1-IL12 ICV exhibit an increase in the percentage of rejection when challenged with RMA-S tumour cells.
Figure 17:
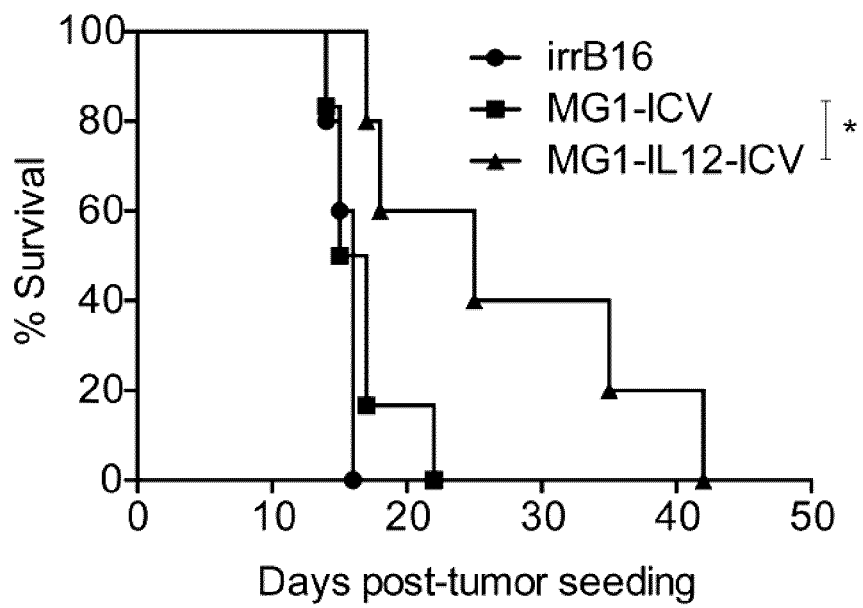
FIG. 17 shows an increase in survival of mice with peritoneal B16F10 tumours that have been vaccinated with MG1-IL12 ICV.

Therefore, the authors next sought to assess whether vaccinating mice i.p. with MG1-IL12 ICV could improve clearance of tumors within the peritoneal cavity and promote improved survival. Similar to their previous observations with i.v. vaccination, the authors observed an increased proportion of NK cells (19% vs 49%, p=0.0073) in the peritoneum 24 hours after i.p. vaccination as compared to MG1 ICV (FIG. 14). The infiltrating NK cells also displayed a significant upregulation of the activation marker CD69 indicating that the NK cells accumulating in the peritoneum in MG1-IL12 ICV vaccinated mice were more highly activated (FIG. 15) (18, 19). To complement these findings, an in-vivo NK cell cytotoxicity assay was performed by challenging vaccinated mice with the NK-sensitive RMA-S and parental RMA tumour cell lines to investigate whether the activated NK cells that migrated into the peritoneal cavity were tumorcidal. Following vaccination with MG1-IL12 ICV, tumour cell clearance was significantly improved demonstrating that ICV-mediated recruitment and activation of NK cells can effectively promote tumor cell clearance from the peritoneum (FIG. 16). In support of this conclusion, the protective effect of vaccinating mice bearing B16F10 peritoneal tumors with MG1-IL12 ICV was completely abrogated upon depletion of NK cells further suggesting that the therapeutic benefit of this treatment strategy is dependent upon NK cell recruitment and activation (FIGS. 17 and 18).

NK Cell Activation and Migration in Response to MG1-IL12 ICV is Partly Dependent Upon the Secretion of IP10 from Dendritic Cells.

The data clearly establish for the ability of MG1-IL12 ICV to promote NK cell activation, migration and function, however, it was unclear whether dendritic cells (DCs), a key mediator of NK cell function in vivo were involved in this process. To understand the interaction between NK cells and DC in the presence of MG1-IL12, the authors quantified IFNγ production from splenocytes cultured in the presence of bone marrow derived DCs, which were either untreated or cultured with mock, MG1, or MG1-IL12 infected B16F10 cells. Notably, the authors found that splenocytes cultured with DCs previously exposed to MG1-IL12 ICV resulted in a significant increase in NK cell-specific IFNγ secretion suggesting DCs promote NK cell cytokine secretion (FIGS. 19 and 20). A subsequent step was to investigate the ability of DCs to promote NK cell migration using an in vitro transwell chemotaxis assay. The migration of NK cells across a 5 um membrane was found to be significantly increased by either MG1 ICV or MG1-IL-12 ICV, however MG1-IL12 ICV resulted in a higher percentage of migrating NK cells (FIG. 21). NK cell migration was further increased by media conditioned in the presence of DCs suggesting that DCs provide the stimuli for increased NK cell activation and migration. Next, the authors sought to identify which chemokines commonly secreted by DCs were mediating the observed effects. Despite the inability to detect any effect on MCP-1 (monocytic chemotactic protein-1) and SDF-1 (stromal cell-derived factor-1) secretion, MG1-IL12 ICV was found to induce a significant increase in IP-10 (IFN-inducible Protein-10) (FIG. 22). The neutralization of IP-10 in conditioned media derived from DCs cultured with MG1-IL12 ICV significantly inhibited the migratory capacity of NK cells in vitro confirming its central role (FIG. 23).

MG1-IL12 ICV is Effective in Treating Established Peritoneal Disease in Mice.

Together the findings suggest that the MG1-IL12 ICV can significantly slow the outgrowth of B16F10 tumours within the peritoneal compartment by stimulating the recruitment of activated NK cells. Since peritoneal carcinomatosis is a common presentation for late stage gastrointestinal and gynecological malignancies, the authors of the present disclosure sought to determine whether the MG1-IL12 ICV could provide therapeutic benefit in a clinically relevant model of colon cancer (CT26) with peritoneal disease at time of treatment. To accomplish this BALB/c mice were seeded with CT26 tumour cells (FIG. 24). Three days later mice were treated with a single dose of irradiated cells alone, virus alone or the infected cell vaccines. Mice treated with irradiated CT26 cells, MG1, MG1-IL12 and MG1 ICV all had significantly lower median survival times and increased peritoneal tumour burden in comparison to mice receiving MG1-IL12 ICV (>90% 26 cured/28 of mice survived have survived >200 days, FIGS. 24 and 25). Interestingly, the cured mice developed a long lasting immunity such that when the surviving mice were re-challenged with $5 \times 10^5$ CT26 cells on the flank, 148 days after treatment, they rejected the tumors (5/5 mice). However, this anti-tumor memory immune response was specific to CT26 tumors and all mice developed tumors (5/5 mice) when challenged with syngeneic 4T1 tumor cells on the opposite flank. Surprisingly, the route of vaccination plays an import role in MG1-IL12 ICV conferred efficacy, in that treatment given intraperitoneally has superior efficacy compared to intravenous or subcutaneous injections (FIG. 39).

Next, the authors sought to measure the effects of treatment in established bulky tumours. Between day 10 and 17 following implantation, tumors were visualized by MRI and mice bearing significant tumour masses (Class 1>8 mm and Class 2>3 mm) were randomly allocated into a treatment group prior to treatment with 6 doses of irradiated cells, MG1 ICV or MG1-IL12 ICV administered over a two week period (FIG. 26). Despite the lethal tumour burden, evident by the loss of all animals treated with irradiated cells by day 15, MG1-IL12 ICV provided complete protection (21/21 survived>80 days, study ongoing). Strikingly, follow-up MRI scans which confirmed the presence of large tumour masses at the early stages of treatment were dramatically reduced at later time points (FIG. 27). Collectively, these results demonstrate that MG1-IL12 ICV is an effective approach for promoting the clearance of large, established tumours within the peritoneum in a murine model of peritoneal carcinomatosis.

MG1-IL-12 ICV Enhances Human NK Cell Cytoxicity and Migratory Capacity.

Given the fact that murine p40 and p35 subunits of IL-12 share 70% and 60% homology with their human counterparts respectively, they are able to functionally activate human NK and T cells (20). The authors next sought to confirm that the vaccine could elicit a similar effect on human NK cells ex vivo. To accomplish this, irradiated SW620 colon cancer cells were infected with MG1 or MG1-IL12 and cultured with peripheral blood mononuclear cells (PBMCs) isolated from a healthy donor as part of a (Perioperative Blood Collection Protocol approved by the Ottawa Health Science Network Research Ethics Board #2011884). In agreement with previous findings, MG1-IL12 ICV resulted in a significant increase in the expression of CD69, an established marker of NK cell activation, in the NK cell (CD56$^+$ CD3$^-$) subset of PBMCs (FIG. 28). In addition, IP-10 chemotactic protein secretion was also significantly increased in the supernatant of PBMCs co-culture with MG1-IL12 ICV. This supernatant enhanced the migration of NK cells in the ex vivo transwell system suggesting that MG1-IL12 ICV vaccine elicits similar responses from NK cells of human and murine origin (FIGS. 29 and 30). Finally, stimulating PBMCs with MG1-IL12 ICV resulted in an increased cytotoxic activity towards K562 target tumour cells suggesting that the activation and enhanced migratory capacity of human NK cells cultured in the presence of MG1-IL12 ICV is associated with increased ability of to eradicate tumour cells (FIGS. 31, 32, 35, 36, 37 and 38). Together these results provide support for the hypothesis that autologous infected tumour cell vaccines may provide a much needed therapeutic benefit in the treatment of patients with PC.

While the above examples demonstrate the efficacy of a particular Maraba virus in mice, the authors believe that Maraba viruses and ICVs according to the present disclosure will also address or ameliorate one or more shortcomings involved with oncolytic virus treatment of cancer in humans.

Peritoneal carcinamatosis is used as an example of a cancer presentation that can be treated using a Maraba virus according to the present disclosure. The authors believe that other tumour types, and tumours in other locations, would also be amenable to treatment with Maraba viruses and ICVs according to the present disclosure.

In the preceding description, for purposes of explanation, numerous details are set forth in order to provide a thorough understanding of the examples. However, it will be apparent to one skilled in the art that these specific details are not required. Accordingly, what has been described is merely illustrative of the application of the described examples and numerous modifications and variations are possible in light of the above teachings.

Since the above description provides examples, it will be appreciated that modifications and variations can be effected to the particular examples by those of skill in the art. Accordingly, the scope of the claims should not be limited by the particular examples set forth herein, but should be construed in a manner consistent with the specification as a whole.

REFERENCES 1. de Gruijl T D, van den Eertwegh A J, Pinedo H M, Scheper R J: Whole-cell cancer vaccination: from autologous to allogeneic tumor- and dendritic cell-based vaccines. *Cancer Immunol Immunother* 2008, 57(10):1569-1577.
2. Chiang C L, Coukos G, Kandalaft L E: Whole Tumor Antigen Vaccines: Where Are We? *Vaccines* (Basel) 2015, 3(2):344-372.
3. Srivatsan S, Patel J M, Bozeman E N, Imasuen I E, He S, Daniels D, Selvaraj P: Allogeneic tumor cell vaccines: the promise and limitations in clinical trials. *Hum Vaccin Immunother* 2014, 10(1):52-63.
4. Campbell C T, Gulley J L, Oyelaran O, Hodge J W, Schlom J, Gildersleeve J C: Humoral response to a viral glycan correlates with survival on PROSTVAC-VF. *Proc Natl Acad Sci USA* 2014, 111(17):E1749-1758.
5. Tugues S, Burkhard S H, Ohs I, Vrohlings M, Nussbaum K, Vom Berg J, Kulig P, Becher B: New insights into IL-12-mediated tumor suppression. *Cell Death Differ* 2015, 22(2):237-246.
6. Brun J, McManus D, Lefebvre C, Hu K, Falls T, Atkins H, Bell J C, McCart J A, Mahoney D, Stojdl D F: Identification of genetically modified Maraba virus as an oncolytic rhabdovirus. *Mol Ther* 2010, 18(8):1440-1449.
7. Mohamed F, Cecil T, Moran B, Sugarbaker P: A new standard of care for the management of peritoneal surface malignancy. *Curr Oncol* 2011, 18(2):e84-96.
8. Aoyagi T, Terracina K P, Raza A, Takabe K: Current treatment options for colon cancer peritoneal carcinomatosis. *World J Gastroenterol* 2014, 20(35):12493-12500.
9. Labbe A, Nelles M, Walia J, Jia L, Furlonger C, Nonaka T, Medin J A, Paige C J: IL-12 immunotherapy of murine leukaemia: comparison of systemic versus gene modified cell therapy. *J Cell Mol Med* 2009, 13(8B):1962-1976.
10. Vaillant J C, Nordlinger B, Deuffic S, Arnaud J P, Pelissier E, Favre J P, Jaeck D, Fourtanier G, Grandjean J P, Marre P et al: Adjuvant intraperitoneal 5-fluorouracil in high-risk colon cancer: A multicenter phase III trial. *Ann Surg* 2000, 231(4):449-456.
11. Mortarini R, Borri A, Tragni G, Bersani I, Vegetti C, Bajetta E, Pilotti S, Cerundolo V, Anichini A: Peripheral burst of tumor-specific cytotoxic T lymphocytes and infiltration of metastatic lesions by memory CD8+ T cells in melanoma patients receiving interleukin 12. *Cancer Res* 2000, 60(13):3559-3568.
12. Lutz M B, Kukutsch N, Ogilvie A L, Rossner S, Koch F, Romani N, Schuler G: An advanced culture method for generating large quantities of highly pure dendritic cells from mouse bone marrow. *J Immunol Methods* 1999, 223(1):77-92.
13. Cheng M, Chen Y, Xiao W, Sun R, Tian Z: NK cell-based immunotherapy for malignant diseases. *Cell Mol Immunol* 2013, 10(3):230-252.
14. Ardolino M, Azimi C S, Iannello A, Trevino T N, Horan L, Zhang L, Deng W, Ring A M, Fischer S, Garcia K C et al: Cytokine therapy reverses NK cell anergy in MHC-deficient tumors. *J Clin Invest* 2014, 124(11):4781-4794.
15. Lemay C G, Rintoul J L, Kus A, Paterson J M, Garcia V, Falls T J, Ferreira L, Bridle B W, Conrad D P, Tang V A et al: Harnessing oncolytic virus-mediated antitumor immunity in an infected cell vaccine. *Mol Ther* 2012, 20(9):1791-1799.
16. Power A T, Wang J, Falls T J, Paterson J M, Parato K A, Lichty B D, Stojdl D F, Forsyth P A, Atkins H, Bell J C: Carrier cell-based delivery of an oncolytic virus circumvents antiviral immunity. *Mol Ther* 2007, 15(1):123-130.
17. Watford W T, Moriguchi M, Morinobu A, O'Shea J J: The biology of IL-12: coordinating innate and adaptive immune responses. *Cytokine Growth Factor Rev* 2003, 14(5):361-368.
18. Hara T, Jung L K, Bjorndahl J M, Fu S M: Human T cell activation. Ill. Rapid induction of a phosphorylated 28 kD/32 kD disulfide-linked early activation antigen (EA 1) by 12-o-tetradecanoyl phorbol-13-acetate, mitogens, and antigens. *J Exp Med* 1986, 164(6):1988-2005.
19. Lanier L L, Buck D W, Rhodes L, Ding A, Evans E, Barney C, Phillips J H: Interleukin 2 activation of natural killer cells rapidly induces the expression and phosphorylation of the Leu-23 activation antigen. *J Exp Med* 1988, 167(5):1572-1585.
20. Schoenhaut D S, Chua A O, Wolitzky A G, Quinn P M, Dwyer C M, McComas W, Familletti P C, Gately M K, Gubler U: Cloning and expression of murine IL-12. *J Immunol* 1992, 148(11):3433-3440.

APPENDIX A

Sequences:

SEQ ID NO: 1-Human IL12 p35 subunit
```
mwppgsasqp ppspaaatgl hpaarpvslq crlsmcpars llvatlvll dhlslarnlp   61
vatpdpgmfp clhhsqnllr avsnmlqkar qtlefypcts eeidhedtk dktstveacl   121
pleltknesc lnsretsfit ngsclasrkt sfmmalclss iyedlkmyqv efktmnakll  181
mdpkrqifld qnmlavidel mqalnfnset vpqkssleep dfyktkiklc illhafrira  241
vtidrvmsyl nas
```

SEQ ID NO: 2-Human IL12 p40 subunit
```
mchqqlvisw fslvflaspl vaiwelkkdv yvveldwypd apgemvvltc dtpeedgitw  61
tldqssevlg sgktltiqvk efgdagqytc hkggevlshs lllhkkedg iwstdilkdq   121
kepknktflr ceaknysgrf tcwwlttist dltfsvkssr gssdpqgvtc gaatlsaerv  181
rgdnkeyeys vecqedsacp aaeeslpiev mvdavhklky enytssffir diikpdppkn  241
lqlkplknsr qvevsweypd twstphsyfs ltfcvqvqgk skrekkdrvf tdktsatvic  301
rknasisvra qdryysssws ewasvpcs
```

SEQ ID NO: 3-Mouse IL12 p35 subunit
```
mvsvptasps asssssqcrs smcqsryllf latlallnhl slarvipvsg parclsqsrn  61
llkttddmvk tareklkhys ctaedidhed itrdqtstlk tclplelhkn esclatrets  121
sttrgsclpp qktslmmtlc lgsiyedlkm yqtefqaina alqnhnhqqi ildkgmlvai  181
delmqslnhn getlrqkppv geadpyrvkm klcillhafs trvvtinrvm gylssa
```

SEQ ID NO: 4-Mouse IL12 p40 subunit
```
mcpqkltisw faivllvspl mamwelekdv yvvevdwtpd apgetvnltc dtpeedditw  61
tsdqrhgvig sgktltitvk efldagqytc hkggetlshs hlllhkkeng iwsteilknf  121
knktflkcea pnysgrftcs wlvqrnmdlk fnikssssp dsravtcgma slsaekvtld  181
qrdyekysvs cqedvtcpta eetlpielal earqqnkyen ystsffirdi ikpdppknlq  241
mkplknsqve vsweypdsws tphsyfslkf fvriqrkkek mketeegcnq kgaflvekts  301
tevqckggnv cvqaqdryyn sscskwacvp crvrs
```

What is claimed is:

1. An oncolytic Maraba virus comprising a genome that comprises, from 3' end to 5' end, nucleic acid sequences encoding an N, a P, an M, a G, and an L protein, and one or more nucleic acid sequences that, alone or in combination, are capable of expressing a human interleukin-12 (IL12) protein or a functional portion thereof, wherein the one or more nucleic acid sequences that, alone or in combination, are capable of expressing a human IL12 protein is/are located in the genome between the 3' end and the nucleic acid sequences encoding the N, P, M, G, and L proteins, in between the nucleic acid sequences encoding the N and the P proteins, in between the nucleic acid sequences encoding the P and the M proteins, in between the nucleic acid sequences encoding the M and the G, or between the '5 end and the nucleic acid sequences encoding the N, P, M, G and L proteins.

2. The Maraba virus of claim 1, wherein the virus comprises a substitution at amino acid 242 of the wild type G protein.

3. The Maraba virus of claim 2, wherein the amino acid at position 242 is an arginine.

4. The Maraba virus of claim 1, wherein the virus comprises a substitution at amino acid 123 of the wild type M protein.

5. The Maraba virus of claim 4, wherein the amino acid at position 123 is a tryptophan.

6. The Maraba virus of claim 3, wherein the Maraba virus is the MG1 Maraba virus.

7. The Maraba virus of claim 1, wherein the human IL12 protein comprises an amino acid sequence that is at least 80% identical to the wild type human IL12 sequence.

8. The Maraba virus of claim 7, wherein the human IL12 protein comprises an amino acid sequence that is at least 90% identical to the wild type human IL12 sequence.

9. The Maraba virus of claim 8, wherein the human IL12 protein comprises an amino acid sequence that is identical to the wild type human IL12 sequence.

10. The Maraba virus of claim 1, wherein the human IL12 protein comprises the p40 and p35 subunits.

11. The Maraba virus of claim 10, wherein the p40 protein comprises the amino acid sequence that is at least 80% identical to the amino acid sequence of SEQ ID NO: 2.

12. The Maraba virus of claim 11, wherein the p40 protein comprises the amino acid sequence of SEQ ID NO: 2.

13. The Maraba virus of claim 10, wherein the p35 protein comprises the amino acid sequence that is at least 80% identical to the amino acid sequence of SEQ ID NO: 1.

14. The Maraba virus of claim 10, wherein the p35 protein comprises the amino acid sequence of SEQ ID NO: 1.

15. The Maraba virus of claim 1, wherein the functional portion of the IL12 protein is a portion that is capable of stimulating the growth of T cells or NK cells.

16. The Maraba virus of claim 1, wherein the functional portion of the IL12 protein is capable of stimulating the production of IFN-gamma.

17. A method for treating a cancer in a patient, the method comprising administering to the patient the oncolytic Maraba virus of claim 1.

18. The method of claim 17, wherein the virus comprises a substitution at amino acid 242 of the wild type G protein.

19. The method of claim 18, wherein the amino acid at position 242 is an arginine.

20. The method of claim 19, wherein the virus comprises a substitution at amino acid 123 of the wild type M protein.

21. The method of claim 20, wherein the amino acid at position 123 is a tryptophan.

22. The method of claim 21, wherein the Maraba virus is the MG1 Maraba virus.

23. The method of claim 22, wherein the human IL12 protein comprises an amino acid sequence that is at least 80% identical to the wildtype human IL12 sequence.

24. The method of claim 23, wherein the human IL12 protein comprises an amino acid sequence that is at least 90% identical to the wild type human IL12 sequence.

25. The method of claim 24, wherein the human IL12 protein comprises an amino acid sequence that is identical to the wild type human IL12 sequence.

26. The method of claim 25, wherein the human IL12 protein comprises the p40 and p35 subunits.

27. The method of claim 26, wherein the p40 protein comprises the amino acid sequence that is at least 80% identical to the amino acid sequence of SEQ ID NO: 2.

28. The method of claim 27, wherein the p40 protein comprises the amino acid sequence of SEQ ID NO: 2.

29. The method of claim 26, wherein the p35 protein comprises the amino acid sequence that is at least 80% identical to the amino acid sequence of SEQ ID NO: 1.

30. The method of claim 29, wherein the p35 protein comprises the amino acid sequence of SEQ ID NO: 1.

31. The method of claim 17, wherein the functional portion of the IL12 protein is a portion that is capable of stimulating the growth of T cells or NK cells.

32. The method of claim 17, wherein the functional portion of the IL12 protein is capable of stimulating the production of IFN-gamma.

33. The method of claim 17, wherein the virus is administered intravenously, intraperitonealy, intrathecally, intracranially, subcutaneously or intrathoracically.

34. The method of claim 33, wherein the virus is administered intravenously.

* * * * *

SEQUENCE LISTING

<160> NUMBER OF SEQ ID NOS: 4

<210> SEQ ID NO 1
<211> LENGTH: 253
<212> TYPE: PRT
<213> ORGANISM: Homo sapiens

<400> SEQUENCE: 1

```
Met Trp Pro Pro Gly Ser Ala Ser Gln Pro Pro Pro Ser Pro Ala Ala
1               5                   10                  15

Ala Thr Gly Leu His Pro Ala Ala Arg Pro Val Ser Leu Gln Cys Arg
            20                  25                  30

Leu Ser Met Cys Pro Ala Arg Ser Leu Leu Leu Val Ala Thr Leu Val
        35                  40                  45

Leu Leu Asp His Leu Ser Leu Ala Arg Asn Leu Pro Val Ala Thr Pro
    50                  55                  60

Asp Pro Gly Met Phe Pro Cys Leu His His Ser Gln Asn Leu Leu Arg
65                  70                  75                  80

Ala Val Ser Asn Met Leu Gln Lys Ala Arg Gln Thr Leu Glu Phe Tyr
                85                  90                  95

Pro Cys Thr Ser Glu Glu Ile Asp His Glu Asp Ile Thr Lys Asp Lys
            100                 105                 110

Thr Ser Thr Val Glu Ala Cys Leu Pro Leu Glu Leu Thr Lys Asn Glu
        115                 120                 125

Ser Cys Leu Asn Ser Arg Glu Thr Ser Phe Ile Thr Asn Gly Ser Cys
    130                 135                 140

Leu Ala Ser Arg Lys Thr Ser Phe Met Met Ala Leu Cys Leu Ser Ser
145                 150                 155                 160

Ile Tyr Glu Asp Leu Lys Met Tyr Gln Val Glu Phe Lys Thr Met Asn
                165                 170                 175
```

-continued

Ala Lys Leu Leu Met Asp Pro Lys Arg Gln Ile Phe Leu Asp Gln Asn
            180                 185                 190

Met Leu Ala Val Ile Asp Glu Leu Met Gln Ala Leu Asn Phe Asn Ser
        195                 200                 205

Glu Thr Val Pro Gln Lys Ser Ser Leu Glu Glu Pro Asp Phe Tyr Lys
    210                 215                 220

Thr Lys Ile Lys Leu Cys Ile Leu Leu His Ala Phe Arg Ile Arg Ala
225                 230                 235                 240

Val Thr Ile Asp Arg Val Met Ser Tyr Leu Asn Ala Ser
            245                 250

<210> SEQ ID NO 2
<211> LENGTH: 328
<212> TYPE: PRT
<213> ORGANISM: Homo sapiens

<400> SEQUENCE: 2

Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
            85                  90                  95

Leu Ser His Ser Leu Leu Leu Leu His Lys Lys Glu Asp Gly Ile Trp
        100                 105                 110

Ser Thr Asp Ile Leu Lys Asp Gln Lys Glu Pro Lys Asn Lys Thr Phe
    115                 120                 125

Leu Arg Cys Glu Ala Lys Asn Tyr Ser Gly Arg Phe Thr Cys Trp Trp
130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
            165                 170                 175

Ala Glu Arg Val Arg Gly Asp Asn Lys Glu Tyr Glu Tyr Ser Val Glu
        180                 185                 190

Cys Gln Glu Asp Ser Ala Cys Pro Ala Ala Glu Glu Ser Leu Pro Ile
    195                 200                 205

Glu Val Met Val Asp Ala Val His Lys Leu Lys Tyr Glu Asn Tyr Thr
        210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
            245                 250                 255

Glu Tyr Pro Asp Thr Trp Ser Thr Pro His Ser Tyr Phe Ser Leu Thr
        260                 265                 270

Phe Cys Val Gln Val Gln Gly Lys Ser Lys Arg Glu Lys Lys Asp Arg
    275                 280                 285

Val Phe Thr Asp Lys Thr Ser Ala Thr Val Ile Cys Arg Lys Asn Ala
        290                 295                 300

-continued

Ser Ile Ser Val Arg Ala Gln Asp Arg Tyr Tyr Ser Ser Ser Trp Ser
305                 310                 315                 320

Glu Trp Ala Ser Val Pro Cys Ser
                325

<210> SEQ ID NO 3
<211> LENGTH: 236
<212> TYPE: PRT
<213> ORGANISM: Mus musculus

<400> SEQUENCE: 3

Met Val Ser Val Pro Thr Ala Ser Pro Ser Ala Ser Ser Ser Ser Ser
1               5                   10                  15

Gln Cys Arg Ser Ser Met Cys Gln Ser Arg Tyr Leu Leu Phe Leu Ala
                20                  25                  30

Thr Leu Ala Leu Leu Asn His Leu Ser Leu Ala Arg Val Ile Pro Val
            35                  40                  45

Ser Gly Pro Ala Arg Cys Leu Ser Gln Ser Arg Asn Leu Leu Lys Thr
50                  55                  60

Thr Asp Asp Met Val Lys Thr Ala Arg Glu Lys Leu Lys His Tyr Ser
65                  70                  75                  80

Cys Thr Ala Glu Asp Ile Asp His Glu Asp Ile Thr Arg Asp Gln Thr
                85                  90                  95

Ser Thr Leu Lys Thr Cys Leu Pro Leu Glu Leu His Lys Asn Glu Ser
            100                 105                 110

Cys Leu Ala Thr Arg Glu Thr Ser Ser Thr Arg Gly Ser Cys Leu
            115                 120                 125

Pro Pro Gln Lys Thr Ser Leu Met Met Thr Leu Cys Leu Gly Ser Ile
130                 135                 140

Tyr Glu Asp Leu Lys Met Tyr Gln Thr Glu Phe Gln Ala Ile Asn Ala
145                 150                 155                 160

Ala Leu Gln Asn His Asn His Gln Gln Ile Ile Leu Asp Lys Gly Met
                165                 170                 175

Leu Val Ala Ile Asp Glu Leu Met Gln Ser Leu Asn His Asn Gly Glu
            180                 185                 190

Thr Leu Arg Gln Lys Pro Pro Val Gly Glu Ala Asp Pro Tyr Arg Val
        195                 200                 205

Lys Met Lys Leu Cys Ile Leu Leu His Ala Phe Ser Thr Arg Val Val
210                 215                 220

Thr Ile Asn Arg Val Met Gly Tyr Leu Ser Ser Ala
225                 230                 235

<210> SEQ ID NO 4
<211> LENGTH: 335
<212> TYPE: PRT
<213> ORGANISM: Mus musculus

<400> SEQUENCE: 4

Met Cys Pro Gln Lys Leu Thr Ile Ser Trp Phe Ala Ile Val Leu Leu
1               5                   10                  15

Val Ser Pro Leu Met Ala Met Trp Glu Leu Glu Lys Asp Val Tyr Val
                20                  25                  30

Val Glu Val Asp Trp Thr Pro Asp Ala Pro Gly Glu Thr Val Asn Leu
            35                  40                  45

Thr Cys Asp Thr Pro Glu Glu Asp Asp Ile Thr Trp Thr Ser Asp Gln
50                  55                  60

-continued

```
Arg His Gly Val Ile Gly Ser Gly Lys Thr Leu Thr Ile Thr Val Lys
65              70                  75                  80

Glu Phe Leu Asp Ala Gly Gln Tyr Thr Cys His Lys Gly Gly Glu Thr
                85                  90                  95

Leu Ser His Ser His Leu Leu Leu His Lys Lys Glu Asn Gly Ile Trp
            100                 105                 110

Ser Thr Glu Ile Leu Lys Asn Phe Lys Asn Lys Thr Phe Leu Lys Cys
        115                 120                 125

Glu Ala Pro Asn Tyr Ser Gly Arg Phe Thr Cys Ser Trp Leu Val Gln
    130                 135                 140

Arg Asn Met Asp Leu Lys Phe Asn Ile Lys Ser Ser Ser Ser Ser Pro
145             150                 155                 160

Asp Ser Arg Ala Val Thr Cys Gly Met Ala Ser Leu Ser Ala Glu Lys
                165                 170                 175

Val Thr Leu Asp Gln Arg Asp Tyr Glu Lys Tyr Ser Val Ser Cys Gln
            180                 185                 190

Glu Asp Val Thr Cys Pro Thr Ala Glu Glu Thr Leu Pro Ile Glu Leu
        195                 200                 205

Ala Leu Glu Ala Arg Gln Gln Asn Lys Tyr Glu Asn Tyr Ser Thr Ser
    210                 215                 220

Phe Phe Ile Arg Asp Ile Ile Lys Pro Asp Pro Pro Lys Asn Leu Gln
225             230                 235                 240

Met Lys Pro Leu Lys Asn Ser Gln Val Glu Val Ser Trp Glu Tyr Pro
                245                 250                 255

Asp Ser Trp Ser Thr Pro His Ser Tyr Phe Ser Leu Lys Phe Phe Val
            260                 265                 270

Arg Ile Gln Arg Lys Lys Glu Lys Met Lys Glu Thr Glu Glu Gly Cys
            275                 280                 285

Asn Gln Lys Gly Ala Phe Leu Val Glu Lys Thr Ser Thr Glu Val Gln
    290                 295                 300

Cys Lys Gly Gly Asn Val Cys Val Gln Ala Gln Asp Arg Tyr Tyr Asn
305             310                 315                 320

Ser Ser Cys Ser Lys Trp Ala Cys Val Pro Cys Arg Val Arg Ser
                325                 330                 335
```